United States Patent
Terashima et al.

(10) Patent No.: US 9,819,881 B2
(45) Date of Patent: Nov. 14, 2017

(54) IMAGE OUTPUT APPARATUS, IMAGE OUTPUT METHOD, AND IMAGE OUTPUT SYSTEM

(71) Applicant: PANASONIC INTELLECTUAL PROPERTY MANAGEMENT CO., LTD., Osaka (JP)

(72) Inventors: Yuuji Terashima, Fukuoka (JP); Naomi Shirai, Kanagawa (JP); Keiji Hirata, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 413 days.

(21) Appl. No.: 14/579,086

(22) Filed: Dec. 22, 2014

(65) Prior Publication Data

US 2015/0181137 A1    Jun. 25, 2015

(30) Foreign Application Priority Data

Dec. 25, 2013   (JP) ................. 2013-267109

(51) Int. Cl.
*H04N 5/33* (2006.01)
*G01S 17/89* (2006.01)
(Continued)

(52) U.S. Cl.
CPC ......... *H04N 5/332* (2013.01); *G01N 21/3151* (2013.01); *G01S 7/4802* (2013.01);
(Continued)

(58) Field of Classification Search
CPC ........ G01S 17/10; G01S 17/89; G01S 7/4802; G01N 2021/1793; G01N 21/3151; G01N 2021/3155; H04N 5/332
(Continued)

(56) References Cited

U.S. PATENT DOCUMENTS

2005/0189503 A1* 9/2005 Jamieson ............. G01N 21/251
250/559.4
2008/0319668 A1  12/2008 Welty et al.
(Continued)

FOREIGN PATENT DOCUMENTS

EP   1569007      8/2005
JP   09-210902    8/1997
(Continued)

OTHER PUBLICATIONS

Search Report and Written Opinion dated Apr. 1, 2015 for the related International Patent Application No. PCT/JP2014/006338.
(Continued)

*Primary Examiner* — Nguyen Truong
(74) *Attorney, Agent, or Firm* — Greenblum & Bernstein, P.L.C.

(57) ABSTRACT

A detection camera includes an imaging optical unit and a light receiving unit that acquire image data, a first detection processing unit that detects a specified substance, a second detection processing unit that acquires distance information from the imaging optical unit to the specified substance, and a display control unit that outputs display data in which information regarding the specified substance is combined with the image data in a case where the distance information is in a detection target distance range.

16 Claims, 19 Drawing Sheets

(51) Int. Cl.
  *G01S 7/48* (2006.01)
  *G01N 21/31* (2006.01)
  *G01S 17/10* (2006.01)
  *G01N 21/17* (2006.01)

(52) U.S. Cl.
  CPC ...... *G01S 17/89* (2013.01); *G01N 2021/1793* (2013.01); *G01N 2021/3155* (2013.01); *G01S 17/10* (2013.01)

(58) Field of Classification Search
  USPC ........................................................ 348/162
  See application file for complete search history.

(56) References Cited

U.S. PATENT DOCUMENTS

| | | | |
|---|---|---|---|
| 2010/0194574 A1* | 8/2010 | Monk | G01N 21/53 340/627 |
| 2013/0182114 A1 | 7/2013 | Zhang et al. | |
| 2013/0271752 A1 | 10/2013 | Bellian et al. | |

FOREIGN PATENT DOCUMENTS

| | | |
|---|---|---|
| JP | 2011-243862 | 12/2011 |
| WO | 2010/088049 | 8/2010 |

OTHER PUBLICATIONS

Rusch P et al: "3-D Reconstruction of Gas Clouds by Scanning Imaging IR Spectroscopy and Tomography", IEEE Sensors Journal, IEEE Service Center, New York, NY, US, vol. 10, No. 3, Feb. 24, 2010 (Feb. 24, 2010), pp. 599-603, XP011303533, ISSN: 1530-437X.

Guo Huadong et al: "A new airborne earth observing system and its applications", Igarss 2001. IEEE 2001 International Geoscience and Remote Sensing Symposium. Sydney, Australia, Jul. 9-13, 2001; [IEEE International Geoscience and Remote Sensing Symposium], New York, NY : IEEE, US, vol. 1, Jul. 9, 2001 (Jul. 9, 2001), pp. 549-551, XP010573185, ISBN: 978-0-7803-7031-9.

\* cited by examiner

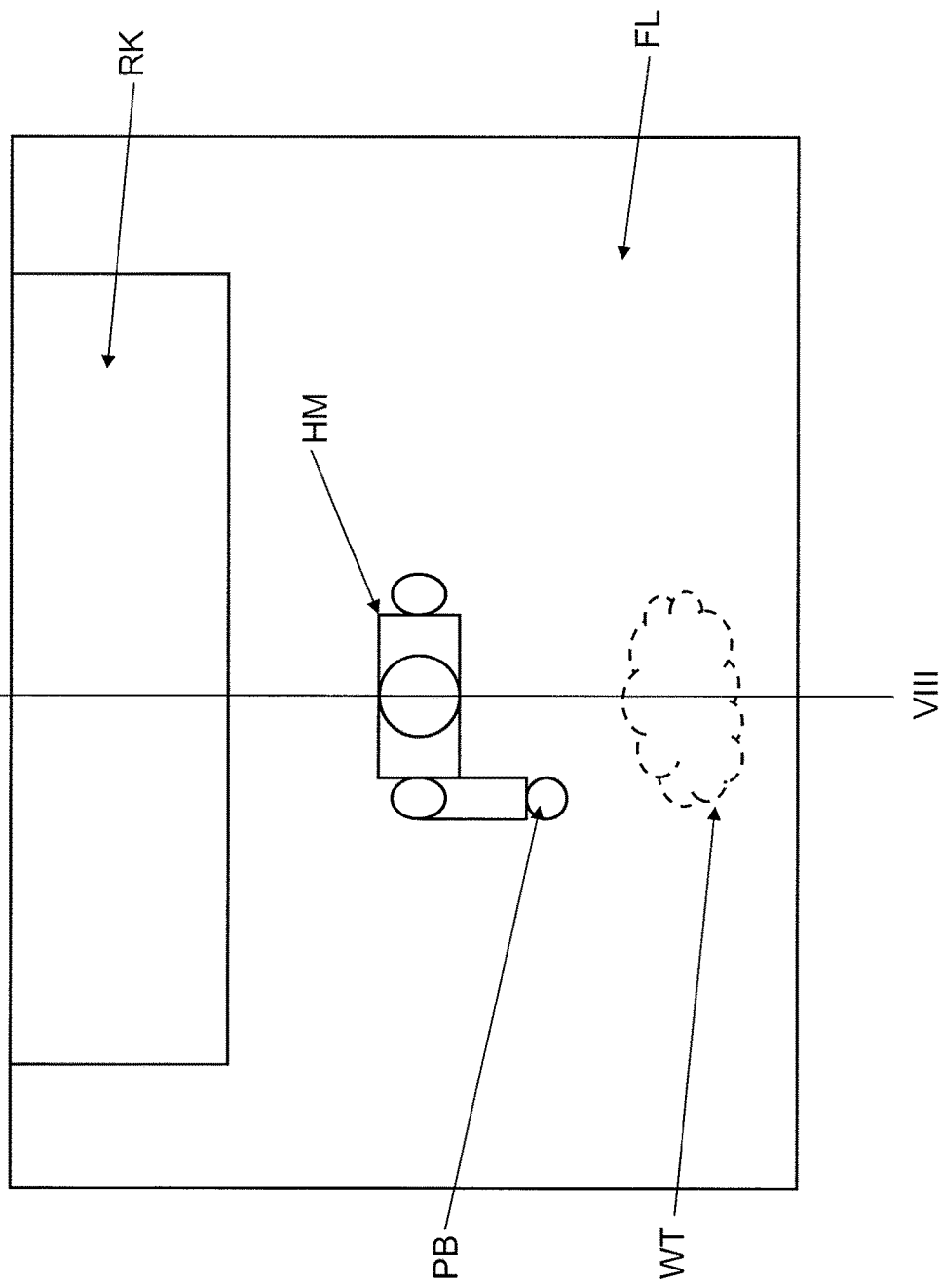

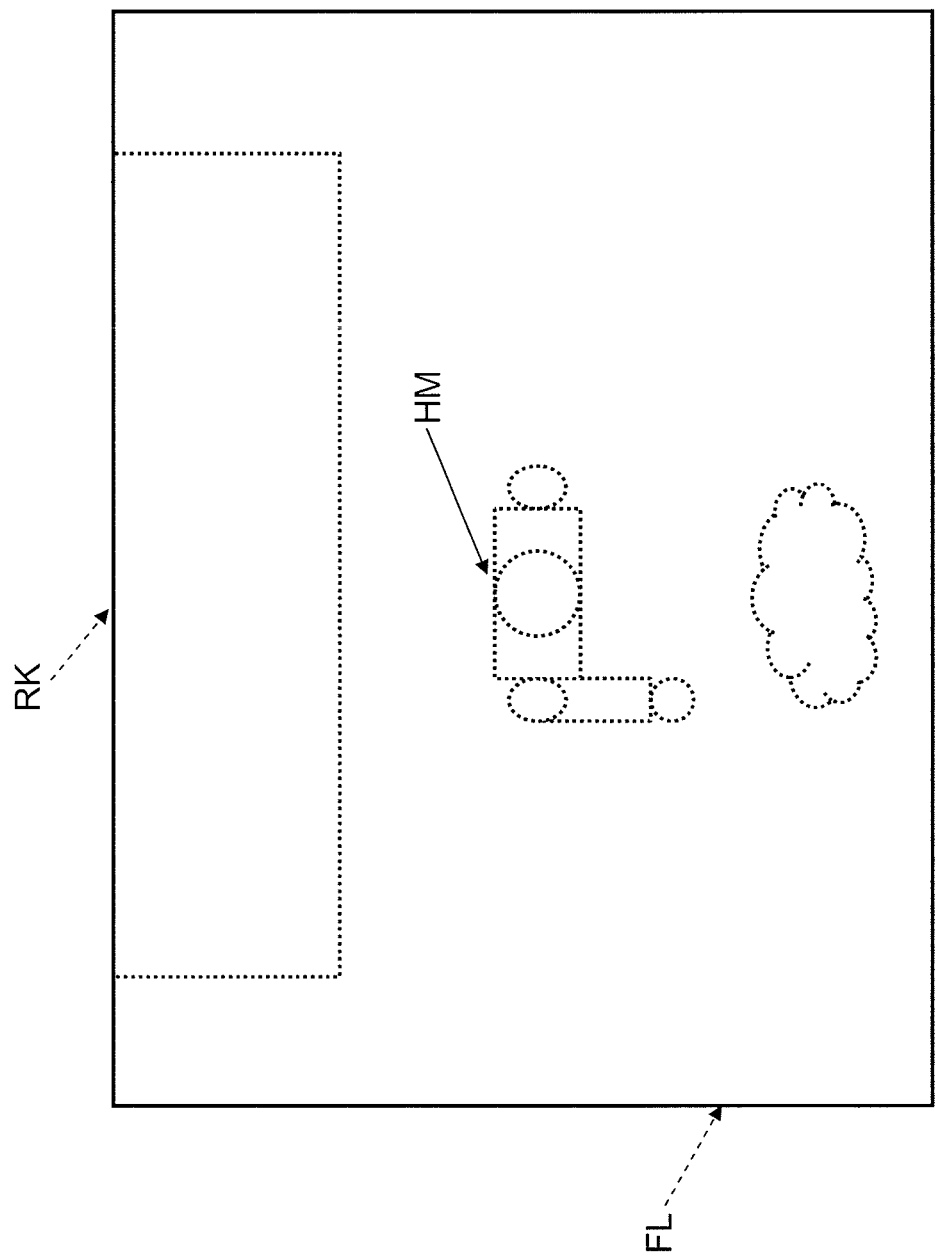

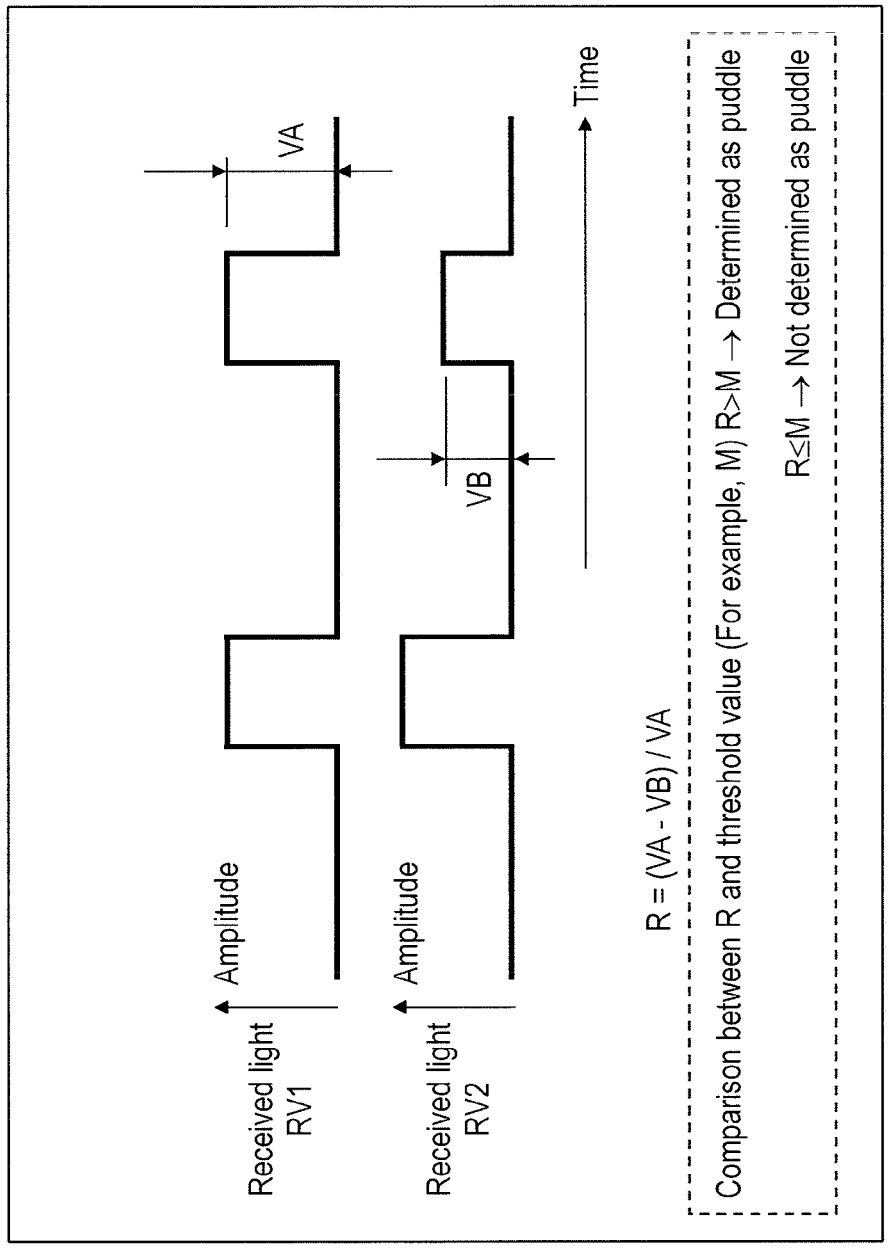

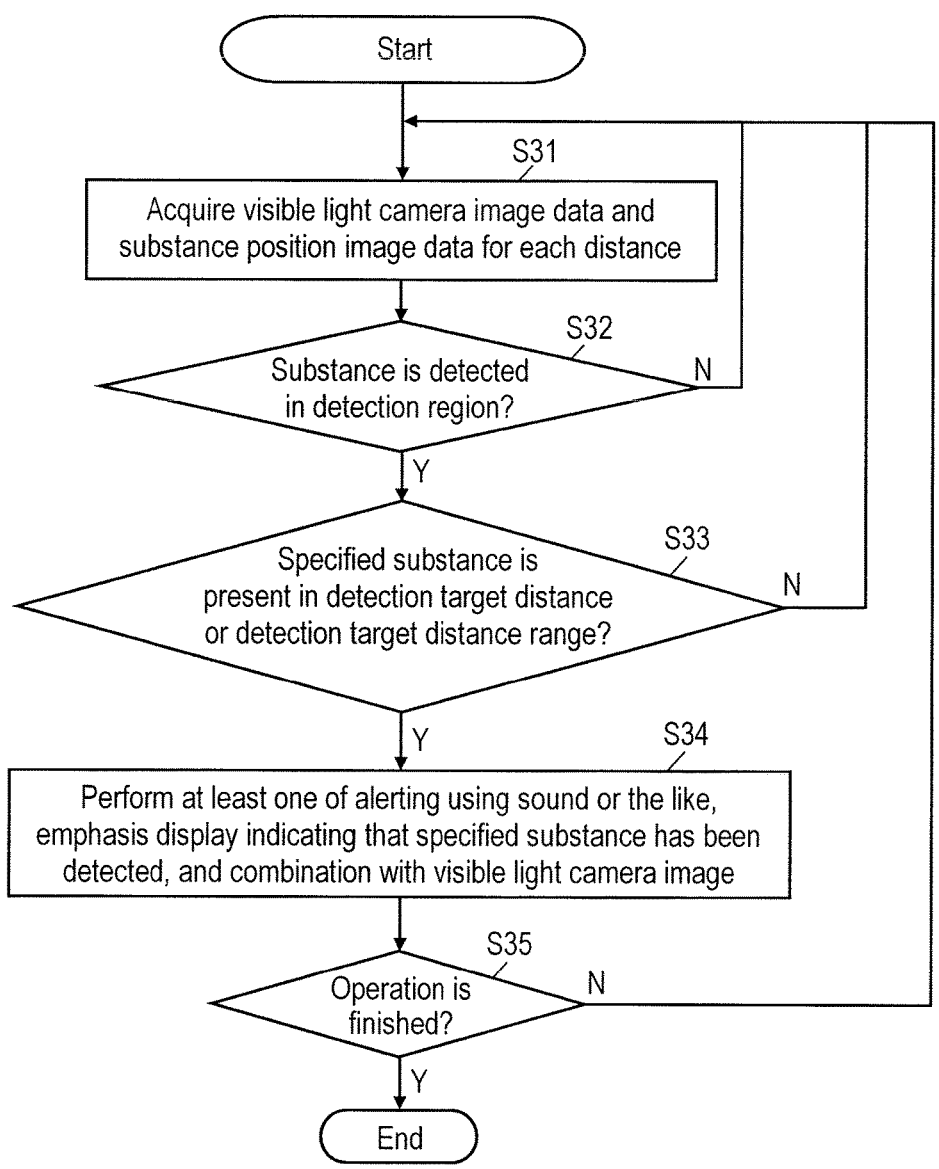

IMAGE OUTPUT APPARATUS, IMAGE OUTPUT METHOD, AND IMAGE OUTPUT SYSTEM

BACKGROUND OF THE INVENTION

1. Field of the Invention

The present invention relates to an image output apparatus, an image output method, and an image output system, for outputting image data.

2. Description of the Related Art

In the related art, as a method of detecting whether or not water is contained in an object, there is a method in which infrared light with a wavelength band which is absorbed by water and infrared light with a wavelength band in which absorption of the water slightly changes are sequentially applied to an object to be detected, and the detection is performed on the basis of the intensity of each beam of infrared light reflected from the object to be detected.

For example, in a water content detection device disclosed in FIG. 2 of Japanese Patent No. 3466360, an object to be detected is sequentially irradiated with light which has a peak of spectral sensitivity on a side (for example, 1.3 µm) shorter than an absorptive wavelength band of water, light which has a peak of spectral sensitivity in the absorptive wavelength band (for example, 1.45 µm) of the water, and light which has a peak of spectral sensitivity on a side (for example, 1.55 µm) longer than the absorptive wavelength band of the water. The water content detection device determines the water content of the object to be detected on the basis of each beam of light reflected from the object to be detected during irradiation with light with a wavelength of 1.3 µm, during irradiation with both light with a wavelength of 1.3 µm and light with a wavelength of 1.45 µm, during irradiation with light with a wavelength of 1.45 µm, during irradiation with light with a wavelength of 1.45 µm and light with a wavelength of 1.55 µm, and during irradiation with light with a wavelength of 1.55 µm.

As a light receiving element used in this water content detection device, an indium-gallium-arsenide (InGaAs) based photodiode is used, and the light reception sensitivity of the light receiving element is 0.7 µm to 1.7 µm. Wavelengths of light beams applied by the water content detection device are 1.3 µm, 1.45 µm, and 1.55 µm. In the water content detection device, a charged coupled device (CCD) or a complementary metal oxide semiconductor (CMOS) which has a peak of spectral sensitivity in the wavelengths (for example, 0.4 µm to 0.7 µm) of visible light is not used.

In the water content detection device, in a case where the water content detection device determines that the water content ratio of the object to be detected is not in a predetermined range, a display indicating abnormality is performed on a display unit. However, it is difficult to determine at which position the water is detected in a visible light image (for example, an image captured by an existing monitoring camera).

SUMMARY OF THE INVENTION

An object of the present invention is to provide an image output apparatus, an image output method, and an image output system, capable of improving detection accuracy of a specified substance in a predetermined detection region by combining a detection result of the specified substance in the predetermined detection region with visible light image data and outputting the obtained result.

According to the present invention, there is provided an image output apparatus including: a detection unit that detects a specified substance; and a combining unit that outputs display data in which information regarding the specified substance is combined with the image data in a case where the specified substance is detected at a predetermined position.

According to the present invention, there is provided an image output method for an image apparatus, the method including: detecting a specified substance; acquiring image data; acquiring distance information from the image output apparatus to the specified substance; and outputting display data in which information regarding the specified substance is combined with the image data in a case where the distance information is within a predetermined range.

According to the present invention, there is provided an image output system including an image output apparatus, and an external connection apparatus. In addition, the image output apparatus includes: a detection unit that detects a specified substance; an imaging unit that acquires image data; an acquisition unit that acquires distance information from the imaging unit to the specified substance; and a combining unit that outputs display data in which information regarding the specified substance is combined with the image data in a case where the distance information is within a predetermined range which is input by the external connection apparatus.

BRIEF DESCRIPTION OF DRAWINGS

FIG. 6 is a diagram illustrating an example of visible light camera image data generated by the visible light camera of the detection camera of the present exemplary embodiment;

FIG. 14 is a diagram illustrating an example of substance position image data indicating a substance detection result at the distance of L2 from the nonvisible light sensor of the detection camera of the present exemplary embodiment;

FIG. 16 is a diagram illustrating a summary of substance detection in the nonvisible light sensor of the detection camera of the present exemplary embodiment;

FIG. 19 is a flowchart illustrating an example of operation procedures for indicating that a specified substance has been detected in a detection target distance range or for generating display data in the display control unit of the visible light camera of the detection camera of the present exemplary embodiment.

DETAILED DESCRIPTION OF THE PREFERRED EMBODIMENT

Hereinafter, an exemplary embodiment (hereinafter, referred to as the "present exemplary embodiment") of an image output apparatus, an image output method, and an image output system according to the present invention will be described with reference to the drawings. The description will be made by using a detection camera as an example of the image output apparatus of the present exemplary embodiment. In addition, the present invention can be expressed as an image output method including respective operations (steps) performed by the image output apparatus, and an image output system provided with the image output apparatus.

Summary of Detection Camera

Figure 1:
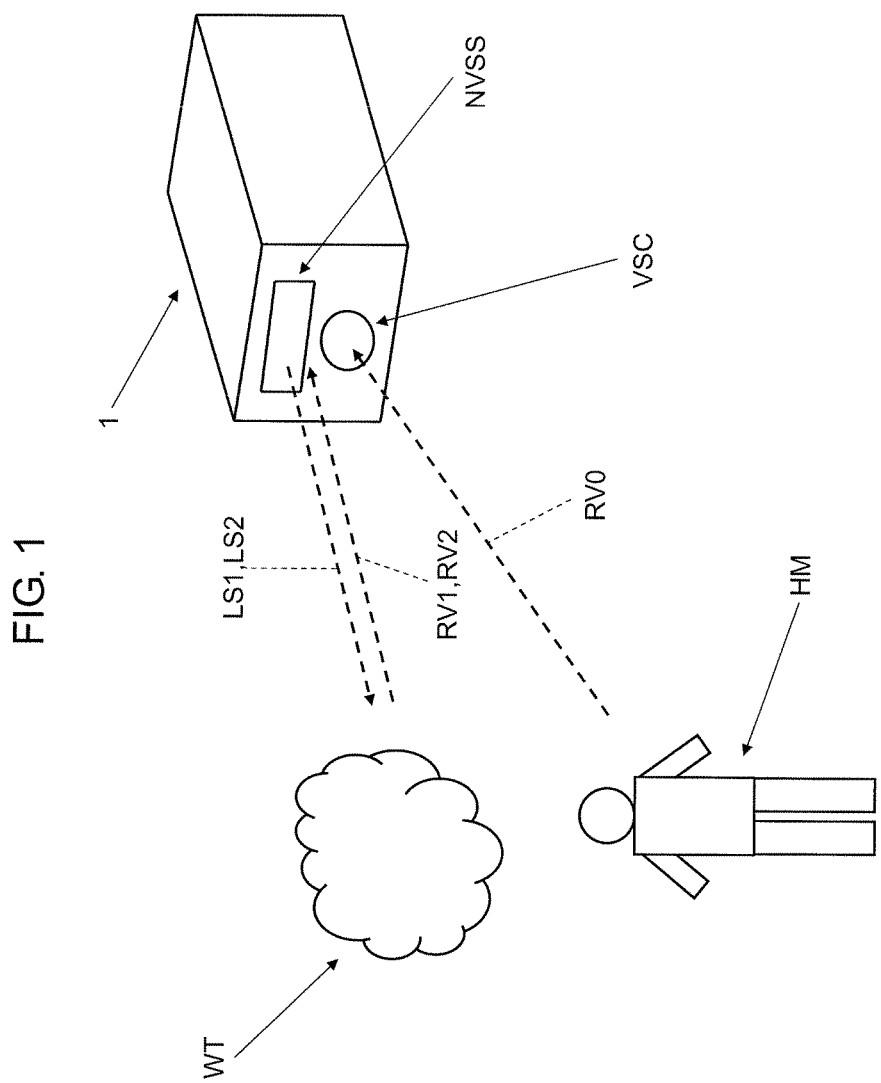
FIG. 1 is a diagram illustrating a summary of a detection camera of the present exemplary embodiment.

FIG. 1 is a diagram illustrating a summary of detection camera 1 of the present exemplary embodiment. Detection camera 1 illustrated in FIG. 1 includes visible light camera VSC and nonvisible light sensor NVSS. Visible light camera VSC images person HM or an object (not illustrated) which is present a predetermined detection region by using reflected light RV0 which is visible light with a predetermined wavelength (for example, 0.4 μm to 0.7 μm) in the same manner as an existing monitoring camera, for example. Hereinafter, output image data which is captured by visible light camera VSC is referred to as "visible light camera image data".

Nonvisible light sensor NVSS projects projection light beams LS1 and LS2 which are nonvisible light beams (for example, infrared light) with predetermined wavelengths (described later) onto the same predetermined detection region as that of visible light camera VSC. Nonvisible light sensor NVSS determines whether or not a specified substance is detected in the detection region by using reflected light beams RV1 and RV2 which are results of projection light beams LS1 and LS2 being reflected from an object to be detected (the specified substance; for example, puddle WT). The specified substance whose presence or absence is determined by nonvisible light sensor NVSS is, for example, a substance which is hardly identified at a glance in the visible light camera image data of visible light camera VSC. Hereinafter, the "puddle WT" will be described as an example, but the specified substance is not limited to puddle WT and may be, for example, a gas (refer to Table 1 described later).

In addition, detection camera 1 generates and outputs display data in which visible light camera image data captured by visible light camera VSC is combined with output image data (hereinafter, referred to as "substance position image data") corresponding to a detection result regarding whether or not a specified substance is present, performed by nonvisible light sensor NVSS, or information regarding the substance position image data. An output destination of the display data from detection camera 1 is an external connection apparatus which is connected to detection camera 1 via, for example, a network (not illustrated), and is camera server CS or communication terminal MT (refer to FIG. 2). The network may be a wired network (for example, an intranet or the Internet), and may be a wireless network (for example, a local area network (LAN)).

Description of Each Constituent Element of Detection Camera

Figure 2:
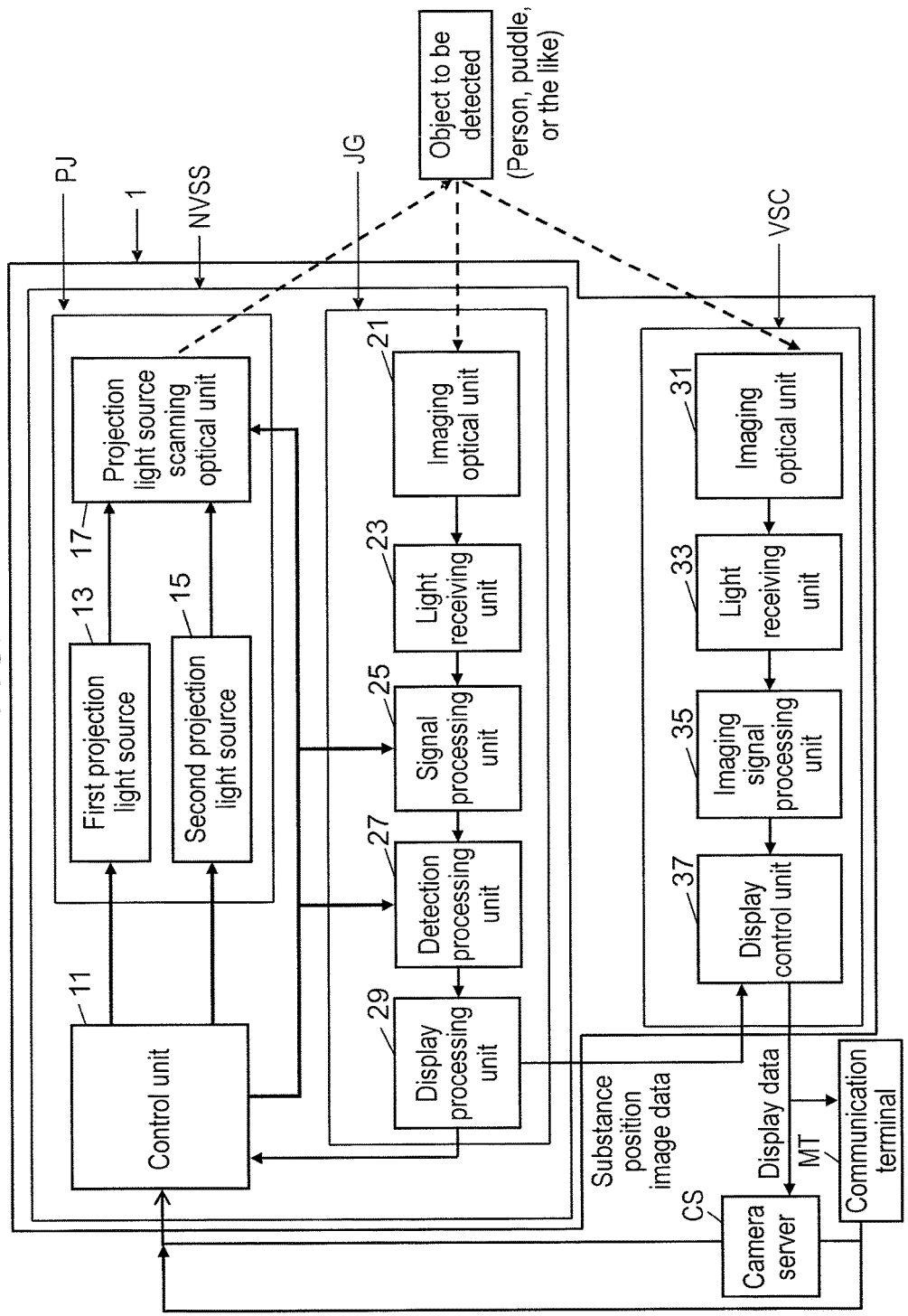
FIG. 2 is a block diagram specifically illustrating an internal configuration of the detection camera of the present exemplary embodiment.

FIG. 2 is a block diagram specifically illustrating an internal configuration of detection camera 1 of the present exemplary embodiment. Detection camera 1 illustrated in FIG. 2 includes nonvisible light sensor NVSS and visible light camera VSC. Nonvisible light sensor NVSS includes control unit 11, projection section PJ, and image determination section JG. Projection section PJ includes first projection light source 13, second projection light source 15, and projection light source scanning optical unit 17. Image determination section JG includes imaging optical unit 21, light receiving unit 23, signal processing unit 25, detection processing unit 27, and display processing unit 29. Visible light camera VSC includes imaging optical unit 31, light receiving unit 33, imaging signal processing unit 35, and display control unit 37.

Description of each constituent element of detection camera 1 will be made in order of control unit 11, nonvisible light sensor NVSS, and visible light camera VSC.

Control unit 11 is constituted by, for example, a central processing unit (CPU), a micro processing unit (MPU), or a digital signal processor (DSP), and performs signal processes for collectively managing operation control of each constituent element of visible light camera VSC or nonvisible light sensor NVSS, data input and output processes with other respective constituent elements, and a data calculation process and data storage process. Control unit 11 includes timing control portion 11*a* described later (refer to FIG. 3).

When control unit 11 as an example of a calculation unit acquires information on a detection target distance which is transmitted due to a user's input operation from camera server CS or communication terminal MT, control unit 11 calculates a detection target distance range of a specified substance which is a detection target of nonvisible light sensor NVSS from detection camera 1, and sets information on the acquired detection target distance or the calculated detection target distance range in signal processing unit 25 or detection processing unit 27, described later. Control unit 11 sets a detection threshold value M of a specified substance which is a detection target of nonvisible light sensor NVSS, in detection processing unit 27 described later. Details of an operation of control unit 11 will be described later with reference to FIG. 4.

Timing control portion 11*a* controls projection timing of first projection light source 13 and second projection light source 15 of projection section PJ. Specifically, in a case where timing control portion 11*a* causes first projection light source 13 and second projection light source 15 to project light, light source scanning timing signal TR is output to first projection light source 13 and second projection light source 15.

Timing control portion 11*a* alternately outputs light source emission signal RF to first projection light source 13 or second projection light source 15 when a predetermined projection cycle starts. Specifically, timing control portion 11*a* outputs light source emission signal RF to first projection light source 13 when an odd-numbered projection cycle starts, and outputs light source emission signal RF to second projection light source 15 when an even-numbered projection cycle starts. Light source emission signal RF is input to distance detection/substance detection processing portion 27*a* of detection processing unit 27, as a signal (reference signal) indicating a start timing of measuring a distance from detection camera 1 to a specified substance (described later).

Next, each constituent element of nonvisible light sensor NVSS will be described.

First projection light source 13 projects (emits) nonvisible light (for example, infrared light) with a predetermined wavelength (for example, 1.1 μm) to a predetermined detection region via projection light source scanning optical unit 17 according to light source emission signal RF from timing control portion 11*a* for each odd-numbered projection cycle (predetermined value) after light source scanning timing signal TR is output from timing control portion 11*a* of control unit 11. In the present exemplary embodiment, projection light LS1 projected from first projection light source 13 is used to measure a distance from detection camera 1 to an object to be detected (specified substance).

However, projection light LS1 may used to detect a specified substance according to a property of the specified substance which is a detection target in the same manner as projection light LS2 projected from second projection light source 15 described later. In other words, detection camera 1 measures a distance from detection camera 1 to the specified substance by using projection light LS1 with a single type of wavelength, and may further determine whether or not the specified substance is detected. Consequently, detection camera 1 can measure distance from detection camera 1 to a specified substance and detect the specified substance by using first projection light source 13 having a single type of wavelength. Therefore, it is possible to minimize an increase in manufacturing cost of detection camera 1.

In addition, whether or not a specified substance is detected may be determined through comparison with a predetermined threshold value. The predetermined threshold value may be a predefined value, may be an arbitrarily set value, and may be a value (for example, a value obtained by adding a predetermined margin to a value of intensity of reflected light acquired in a state in which there is no specified substance) based on the intensity of reflected light in a case where there is no specified substance. In other words, whether or not a specified substance is detected may be determined by comparing substance position image data acquired in a state in which there is no specified substance with substance position image data which is subsequently acquired. As mentioned above, if the intensity of reflected light is acquired in a state in which there is no specified substance, it is possible to set a threshold value suitable for circumstances in which detection camera 1 is installed, as a threshold value for detecting whether or not the specified substance is detected.

Second projection light source 15 projects (emits) nonvisible light (for example, infrared light) with a predetermined wavelength (for example, 1.45 μm) to a predetermined detection region via projection light source scanning optical unit 17 according to light source emission signal RF from timing control portion 11*a* for each even-numbered projection cycle (predetermined value) after light source scanning timing signal TR is output from timing control portion 11*a* of control unit 11. In the present exemplary embodiment, projection light LS2 projected from second projection light source 15 is used to determine whether or not a specified substance is detected in the detection region of detection camera 1. The wavelength 1.45 μm of projection light LS2 is a wavelength which is very suitable for a case where a specified substance which is a detection target is water (the same for water vapor) such as puddle WT.

Consequently, detection camera 1 measures a distance from detection camera 1 to a specified substance by using projection light LS1 with the first wavelength and reflected light RV1 thereof, and uses reflected light RV1 of projection light LS1 with the first wavelength as reference data for detecting the specified substance. Detection camera 1 determines whether or not the specified substance is detected in the predetermined detection region by using projection light LS2 with the second wavelength, reflected light RV2 thereof, and the above-described reference data, that is, reflected light RV1 of projection light LS1 with the first wavelength. Therefore, detection camera 1 can detect a specified substance in a predetermined detection region with high accuracy by using projection light beams with two different types of wavelengths and reflected light beams thereof to measure a distance from detection camera 1 to the specified substance and to detect the specified substance.

Projection light source scanning optical unit 17 scans a predetermined detection region of nonvisible light sensor NVSS with projection light LS1 projected from first projection light source 13 or projection light LS2 projected from second projection light source 15 in a two-dimensional manner. Thus, image determination section JG can measure a distance from detection camera 1 to a specified substance on the basis of reflected light RV1 which is a result of projection light LS1 being reflected from the specified substance, and can determine whether or not the specified substance is detected in the predetermined detection region on the basis of reflected light RV2 which is a result of projection light LS2 being reflected from the specified substance, and the above-described reflected light RV1, that is, reflected light RV1 of projection light LS1 with the first wavelength.

Figure 3:
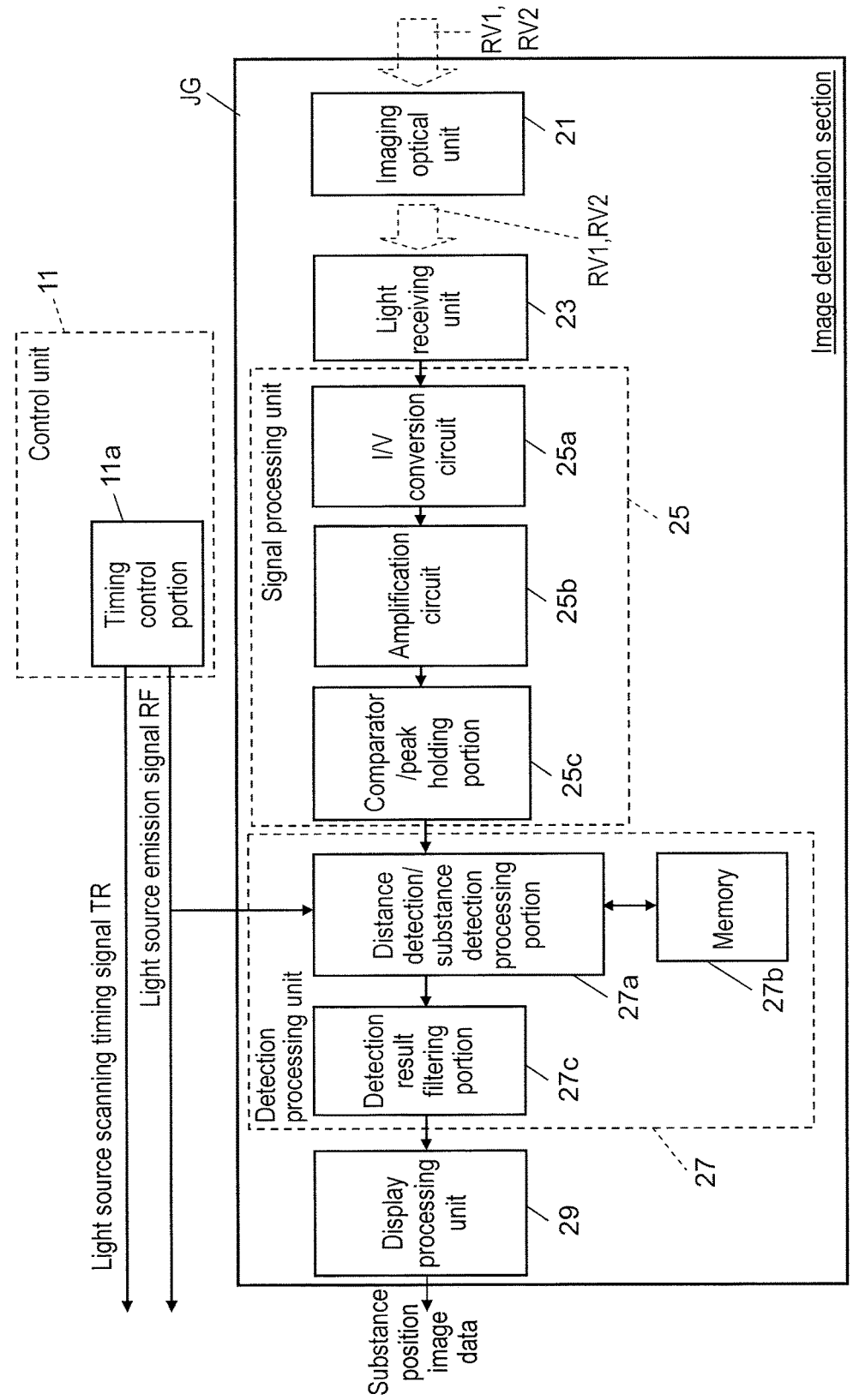
FIG. 3 is a block diagram illustrating details of an internal configuration of an image determination unit of a nonvisible light sensor of the detection camera according to the present exemplary embodiment.

Next, an internal configuration of image determination section JG will be described in detail with reference to FIGS. 2 and 3. FIG. 3 is a block diagram specifically illustrating an internal configuration of image determination section JG of nonvisible light sensor NVSS of detection camera 1 according to the present exemplary embodiment.

Imaging optical unit 21 is constituted by, for example, a lens, collects light (for example, reflected light RV1 or reflected light RV2) which is incident from outside of detection camera 1, and forms an image of reflected light RV1 or reflected light RV2 on a predetermined imaging surface of light receiving unit 23.

Light receiving unit 23 is an image sensor which has a peak of spectral sensitivity for both of the wavelengths of projection light LS1 and projection light LS2. Light receiving unit 23 converts the optical image of reflected light RV1 or reflected light RV2 formed on the imaging surface into an electric signal. An output from light receiving unit 23 is input to signal processing unit 25 as an electric signal (current signal). Imaging optical unit 21 and light receiving unit 23 function as an imaging unit in nonvisible light sensor NVSS.

Signal processing unit 25 includes I/V conversion circuit 25a, amplification circuit 25b, and comparator/peak holding portion 25c. I/V conversion circuit 25a converts the current signal which is an output signal (analog signal) from light receiving unit 23 into a voltage signal. Amplification circuit 25b amplifies a level of the voltage signal which is an output signal (analog signal) from I/V conversion circuit 25a, to a level which can be processed by comparator/peak holding portion 25c.

Comparator/peak holding portion 25c binarizes an output signal from amplification circuit 25b according to a comparison result between the output signal (analog signal) from amplification circuit 25b with a predetermined threshold value, and outputs an obtained result to distance detection/substance detection processing portion 27a. In addition, comparator/peak holding portion 25c includes an analog-digital converter (ADC), detects and holds a peak of an analog-digital (AD) conversion result of the output signal (analog signal) from amplification circuit 25b, and outputs information on the peak to distance detection/substance detection processing portion 27a.

Detection processing unit 27 as an example of a detection unit includes distance detection/substance detection processing portion 27a, memory 27b, and detection result filtering portion 27c. Distance detection/substance detection processing portion 27a measures a distance from detection camera 1 to a specified substance on the basis of an output (binarized signal) from comparator/peak holding portion 25c for reflected light RV1 of projection light LS1 with the first wavelength (for example, 1.1 μm).

Figure 7A:
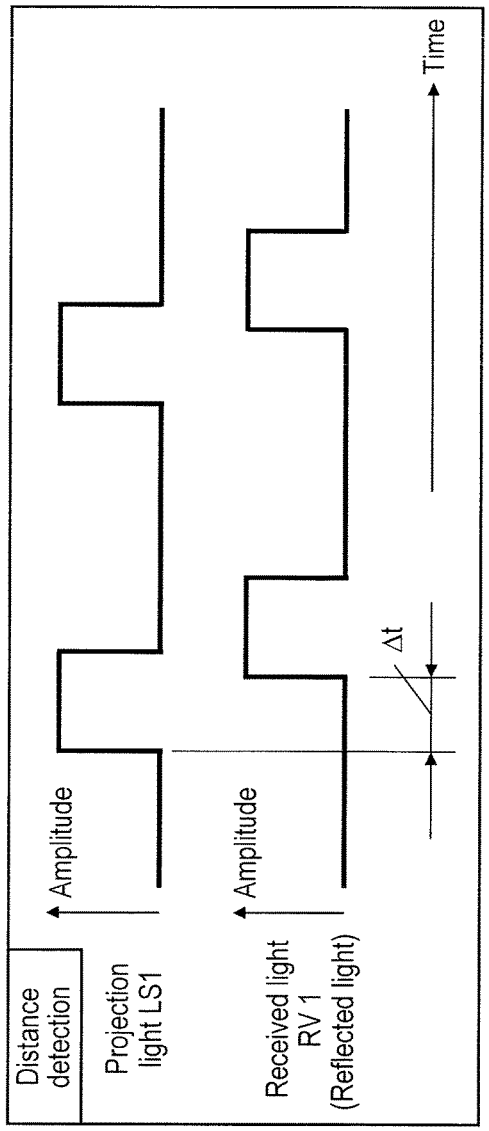
FIG. 7A is a diagram illustrating the principle of distance detection using projection light with a single type of wavelength in the detection camera of the present exemplary embodiment.
Figure 15A:
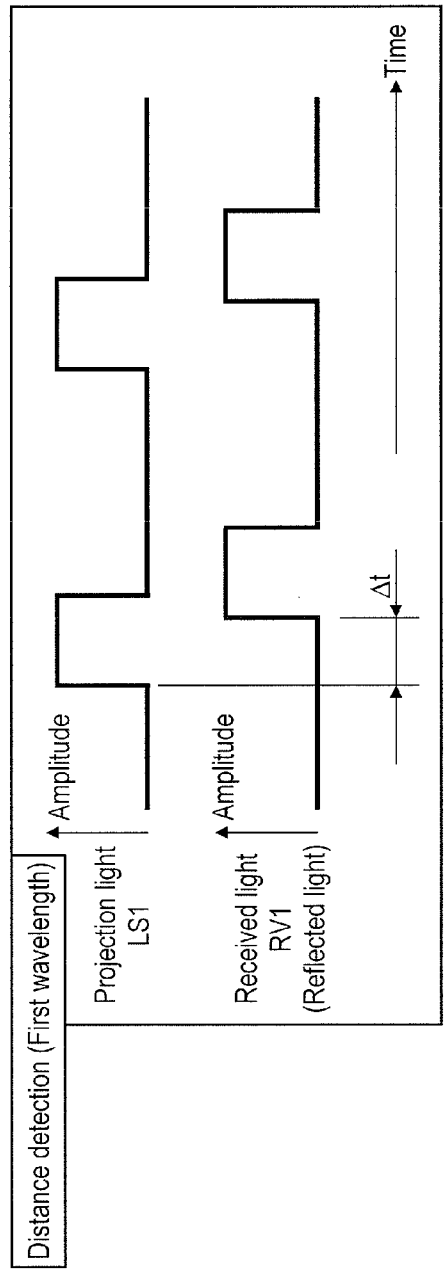
FIG. 15A is a diagram illustrating the principle of distance detection using projection light with a first wavelength of two different types of wavelengths in the detection camera of the present exemplary embodiment.

Specifically, distance detection/substance detection processing portion 27a measures distance D from detection camera 1 to a specified substance on the basis of time difference Δt (refer to FIG. 7A or FIG. 15A) between the time when projection light LS1 is projected and the time when reflected light RV1 is received. FIG. 7A is a diagram illustrating a principle of distance detection using projection light LS1 with a single type of wavelength in detection camera 1 of the present exemplary embodiment. FIG. 15A is a diagram illustrating a principle of distance detection using projection light LS1 with the first wavelength of two types of wavelengths in detection camera 1 of the present exemplary embodiment.

Distance detection/substance detection processing portion 27a determines the time at which light source emission signal RF is input from timing control portion 11a as the time when projection light LS1 is projected, and determines the time at which an output from comparator/peak holding portion 25c is input as the time when reflected light RV1 is received. Distance detection/substance detection processing portion 27a calculates, for example, distance D as "distance D=light speed×(time difference Δt/2)" so as to easily obtain distance D from detection camera 1 to a specified substance. An output from comparator/peak holding portion 25c for reflected light RV1 of projection light LS1 with at least one type of wavelength is required to measure distance D in distance detection/substance detection processing portion 27a. Distance detection/substance detection processing portion 27a outputs information on distance D to detection result filtering portion 27c.

Distance detection/substance detection processing portion 27a determines whether or not a specified substance is detected in the detection region on the basis of an output (peak information) from comparator/peak holding portion 25c for reflected light RV1 of projection light LS1 with the first wavelength and an output (peak information) from comparator/peak holding portion 25c for reflected light RV2 of projection light LS2 with the second wavelength.

Specifically, distance detection/substance detection processing portion 27a temporarily preserves, for example, the output (peak information) from comparator/peak holding portion 25c for reflected light RV1 of projection light LS1 with the first wavelength, in memory 27b, and then waits until the output (peak information) from comparator/peak holding portion 25c for reflected light RV2 of projection light LS2 with the second wavelength is obtained. Distance detection/substance detection processing portion 27a obtains the output (peak information) from comparator/peak holding portion 25c for reflected light RV2 of projection light LS2 with the second wavelength and then refers to memory 27b so as to compare the output (peak information) from comparator/peak holding portion 25c for reflected light RV1 of projection light LS1 with the first wavelength with the output (peak information) from comparator/peak holding portion 25c for reflected light RV2 of projection light LS2 with the second wavelength in the same line of the detection region.

Figure 7B:
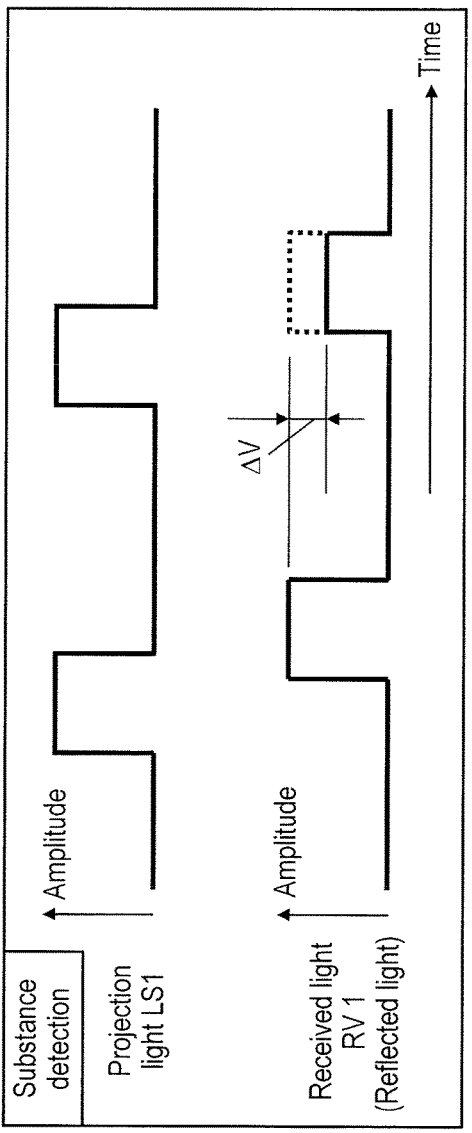
FIG. 7B is a diagram illustrating the principle of substance detection using projection light with a single type of wavelength in the detection camera of the present exemplary embodiment.
Figure 15B:
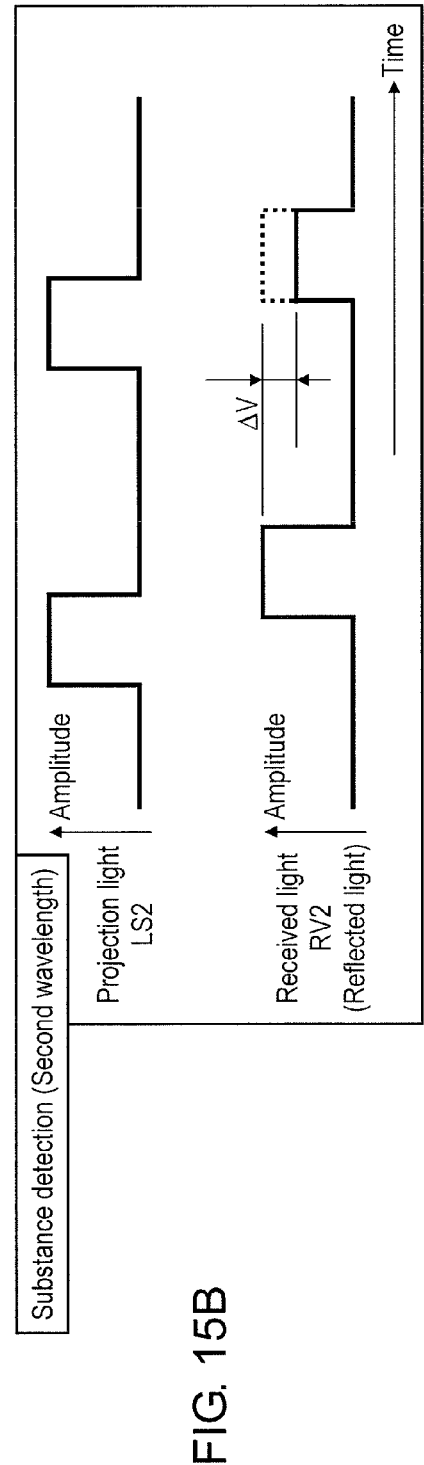
FIG. 15B is a diagram illustrating the principle of substance detection using projection light with a second wavelength of two different types of wavelengths in the detection camera of the present exemplary embodiment.

For example, since projection light LS2 with the second wavelength (for example, 1.45 μm) is absorbed in a location where puddle WT is present, the intensity (amplitude) of reflected light RV1 or reflected light RV2 is attenuated (refer to FIG. 7B or 15B). FIG. 7B is a diagram illustrating a principle of substance detection using projection light LS1 with a single type of wavelength in detection camera 1 of the present exemplary embodiment. FIG. 15B is a diagram illustrating the principle of substance detection using projection light LS2 with the second wavelength of two types of wavelengths in detection camera 1 of the present exemplary embodiment. Therefore, distance detection/substance detection processing portion 27a determines whether or not a specified substance is detected in the detection region on the basis of a comparison result for each line of the detection region, that is, a difference (difference ΔV between the amplitudes) between the intensities of reflected light RV1 and reflected light RV2.

Distance detection/substance detection processing portion 27a may compare ratio R of an amplitude difference (VA−

VB) between amplitude VA of reflected light RV1 of projection light LS1 with the first wavelength and amplitude VB of reflected light RV2 of projection light LS2 with the second wavelength, to the amplitude VA, with the predetermined threshold value M, so as to determine whether or not a specified substance is detected in the detection region (refer to FIG. 16). FIG. 16 is a diagram illustrating a summary of substance detection in nonvisible light sensor NVSS of detection camera 1 of the present exemplary embodiment. Distance detection/substance detection processing portion 27a determines that puddle WT is detected, for example, if R>M, and determines that puddle WT is not detected if R≥M. As mentioned above, distance detection/substance detection processing portion 27a determines whether or not a specified substance is detected in the detection region on the basis of a comparison result between the ratio R of the amplitude difference (VA−VB) to the amplitude VA and the threshold value M, so as to exclude an influence of noise (for example, disturbance light), and thus it is possible to determine whether or not a specified substance is detected with high accuracy.

Memory 27b is constituted by, for example, a random access memory (RAM), and temporarily preserves the output (peak information) from comparator/peak holding portion 25c for reflected light RV1 of projection light LS1 with the first wavelength.

On the basis of the output from distance detection/substance detection processing portion 27a and a predetermined detection target distance or detection target distance range designated by control unit 11, detection result filtering portion 27c filters and extracts information regarding the specified substance of which a distance from detection camera 1 is within the detection target distance or the detection target distance range. Detection result filtering portion 27c outputs information regarding the extraction result in the detection region to display processing unit 29. For example, detection result filtering portion 27c outputs information regarding a detection result of the specified substance on a floor (distance D=L0) of the detection region, to display processing unit 29.

Display processing unit 29 generates substance position image data indicating a position of the specified substance in the detection region for each distance from detection camera 1 by using an output from detection result filtering portion 27c, as an example of the information regarding the specified substance of which a distance from detection camera 1 in the detection region is within the detection target distance or the detection target distance range. Display processing unit 29 outputs the substance position image data including information on the distance from detection camera 1 to the specified substance, to display control unit 37 of visible light camera VSC.

Next, each constituent element of visible light camera VSC will be described.

Imaging optical unit 31 is constituted by, for example, a lens, and collects incident light (for example, reflected light RV0 which is visible light) from outside, which has the detection region of detection camera 1 as an angle of view so as to form an image of reflected light RV0 on a predetermined imaging surface of light receiving unit 33.

Light receiving unit 33 is an image sensor which has a peak of spectral sensitivity for a wavelength (for example, 0.4 μm to 0.7 μm) of visible light. Light receiving unit 33 converts the optical image formed on the imaging surface into an electric signal. An output from light receiving unit 33 is input to imaging signal processing unit 35. Imaging optical unit 31 and light receiving unit 33 function as an imaging unit in visible light camera VSC.

Imaging signal processing unit 35 generates visible light camera image data defined by red, green, and blue (RGB) or YUV (luminance and color difference) which can be recognized by human eyes, by using the electric signal which is an output from light receiving unit 33. Consequently, visible light camera image data which is captured by visible light camera VSC is formed. Imaging signal processing unit 35 outputs the visible light camera image data to display control unit 37.

By the use of the visible light camera image data output from imaging signal processing unit 35 and the substance position image data output from display processing unit 29, display control unit 37 as an example of a combining unit generates display data in which the visible light camera image data is combined with the substance position image data, as an example of the information regarding the specified substance, in a case where the specified substance is detected at a predetermined position of the visible light camera image data.

In addition, in a case where a distance from detection camera 1 to the specified substance is in the detection target distance or the detection target distance range, display control unit 37 generates display data in which the visible light camera image data is combined with the substance position image data, as an example of the information regarding the specified substance. Display control unit 37 transmits the display data, for example, to camera server CS or communication terminal MT via a network so as to make a request for display thereof. Details of the generation process of display data in display control unit 37 will be described later with reference to FIGS. 18 to 20.

Control unit 11 may change the detection target distance or the detection target distance range which is an example of set distance information which is set in detection processing unit 27. This change of the detection target distance range may be automatically performed by control unit 11, and may be performed at any timing by a user using communication terminal MT or the like. Consequently, it is possible to set a suitable detection target distance or detection target distance range according to the environment in which detection camera 1 is installed. The set distance information is, for example, a detection target distance which is set in detection result filtering portion 27c of detection processing unit 27 in advance.

In a case where a detection target distance range is calculated on the basis of information on a detection target distance which is input via camera server CS or communication terminal MT, control unit 11 may change a value of the calculated detection target distance range depending on a value of the detection target distance. In a case where a distance to a detection target is far, the intensity (amplitude) of reflected light attenuates more greatly than in a case where a distance to the detection target is short, and thus the amount of error increases when distance detection/substance detection processing portion 27a detects distance. Control unit 11 preferably increases a detection target distance range to be calculated as a value of an input detection target distance becomes greater. For example, in a case where a detection target distance output from control unit 11 is 3 [m], detection processing unit 27 changes a detection target distance range to 2 to 4 [m]. In a case where a detection target distance output from control unit 11 is 100 [m], detection processing unit 27 changes a detection target distance range 95 to 105 [m]. Consequently, detection camera 1 can set a suitable detection target distance range according to a distance to a detection target. Therefore, display control unit 37 can generate display data as an example of the information regarding a specified substance, and also in consideration of errors according to a length of a detection target distance when detection processing unit 27 detects a distance. Since the detection target distance range is set, detection camera 1 can detect a specified substance even in a case where a distance from detection camera 1 to the specified substance is exactly the same as a detection target distance output from control unit 11.

Camera server CS as an example of an input unit transmits the display data which is output from display control unit 37 to communication terminal MT or one or more external connection apparatuses (not illustrated), and makes a request for display of the display data on a display screen of communication terminal MT or display screens of one or more external connection apparatuses. In addition, camera server CS transmits information on a detection target distance or a detection target distance range of a specified substance, transmitted through a user's input operation on communication terminal MT or one or more external connection apparatuses, to detection camera 1. The information on the detection target distance or the detection target distance range of the specified substance is input to control unit 11. Consequently, camera server CS can input the information on the detection target distance or the detection target distance range of the specified substance designated through the user's input operation, to detection camera 1. The detection target distance range of the specified substance, input from camera server CS to detection camera 1, may be a plurality of ranges, and any set number of plural detection target distance ranges may also be input. Consequently, camera server CS can set a detection target distance range desired by a user, or any set number of detection target distance ranges, in detection camera 1.

Communication terminal MT as an example of an input unit is a portable communication terminal used by a personal user, receives display data transmitted from display control unit 37 via a network (not illustrated), and displays the display data on a display screen (not illustrated) of communication terminal MT. In a case where information on a detection target distance of a specified substance is input through a user's input operation, communication terminal MT transmits information on the detection target distance or the detection target distance range of the specified substance to detection camera 1 via camera server CS or directly. Similarly, the information on the detection target distance or the detection target distance range of the specified substance is input to control unit 11. Consequently, communication terminal MT can input the information on the detection target distance or the detection target distance range of the specified substance, designated through a user's input operation, to detection camera 1 via camera server CS or directly. The detection target distance range of the specified substance, input from communication terminal MT to detection camera 1, may be a plurality of ranges, and any set number of plural detection target distance ranges may also be input. Consequently, communication terminal MT can set a detection target distance range desired by a user, or any set number of detection target distance ranges, in detection camera 1.

In a case where a detection target distance range is input through a user's input operation, control unit 11 may not change the input detection target distance range which is then set in detection processing unit 27. Alternatively, control unit 11 as an example of a calculation unit may calculate a detection target distance range to be set in detection processing unit 27 on the basis of the input detection target distance range, and may set the calculated detection target distance range in detection processing unit 27. For example, in a case where a detection target distance range of 4 to 7 [m] is input through a user's input operation, control unit 11 may change the detection target distance range to 5 to 6 [m] or 3 to 8 [m] which is then set in detection processing unit 27.

Figure 4:
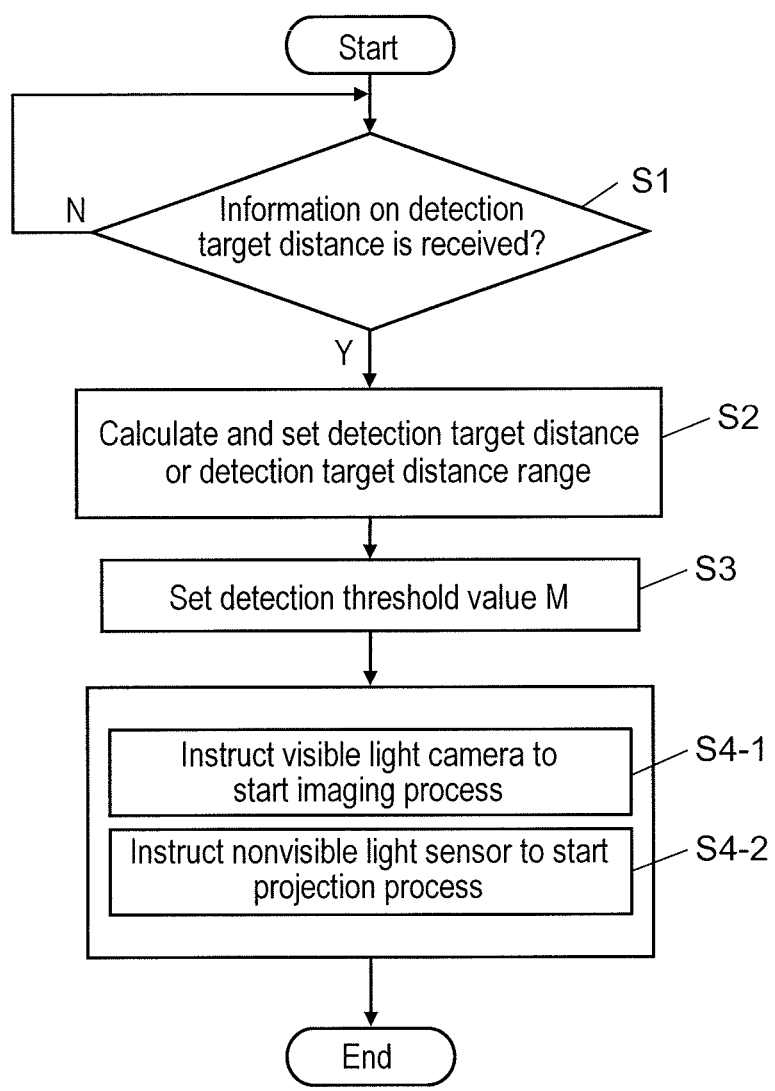
FIG. 4 is a flowchart illustrating an example of an initial operation in a control unit of the nonvisible light sensor of the detection camera of the present exemplary embodiment.

Description of Example of Initial Operation in Control Unit of Nonvisible Light Sensor Next, with reference to FIG. 4, a description will be made of an example of an initial operation in control unit 11 of nonvisible light sensor NVSS of detection camera 1 according to the present exemplary embodiment. FIG. 4 is a flowchart illustrating an example of an initial operation in control unit 11 of nonvisible light sensor NVSS of detection camera 1 according to the present exemplary embodiment.

In FIG. 4, if detection camera 1 receives information on a detection target distance of the specified substance transmitted from camera server CS or communication terminal MT (Y in step S1), control unit 11 acquires the information on the detection target distance of the specified substance. Control unit 11 calculates a detection target distance range of the specified substance which is a detection target of nonvisible light sensor NVSS on the basis of the information on the detection target distance of the specified substance, and sets information on the acquired detection target distance or the calculated detection target distance range in signal processing unit 25 or detection processing unit 27 (step S2).

The information on the detection target distance of the specified substance includes information on a distance or a direction of the specified substance which is present as a detection target in the detection region from detection camera 1, installation condition information of detection camera 1, and the like. The information on the distance from detection camera 1 may be a predefined value, and may be set to any value by a user using communication terminal MT or the like. The installation condition information of detection camera 1 may be set in detection camera 1 in advance, and may be set to any value by the user using communication terminal MT or the like. The installation condition information includes, for example, information on the height (a distance L0 illustrated in FIG. 5) of detection camera 1 from a predetermined surface (for example, a floor FL), a projection angle (for example, an angle or the like formed between floor FL and a projection direction of projection light source scanning optical unit 17) of detection camera 1, an area of a living room where detection camera 1 is installed, or the like. In detection camera 1 to which the installation condition information has been input, for example, control unit 11 may calculate a detection target distance or a detection target distance range of the specified substance on the basis of the installation condition information. Since the installation condition information is set as mentioned above, it is possible to detect a specified substance according to installation circumstances and thus to minimize detection errors.

Control unit 11 may change the detection target distance range calculated in step S2 on the basis of the information on the height of detection camera 1 from the predetermined surface (for example, floor FL). This change of the detection target distance range may be automatically performed by control unit 11, and may be performed at any timing by a user using communication terminal MT or the like. The detection target distance range may not be calculated on the basis of the detection target distance but may be directly input via camera server CS, communication terminal MT, or the like. Alternatively, detection camera 1 may be provided with an input unit which allows a detection target distance or a detection target distance range to be input.

In a case where a distance to a detection target is long, the intensity (amplitude) of reflected light attenuates more greatly than in a case where a distance to the detection target is short, and thus an error increases when distance detection/substance detection processing portion 27*a* detects a distance. For this reason, control unit 11 preferably increases a detection target distance range to be calculated as input height information indicates a greater value. Consequently, detection camera 1 changes a detection target distance range depending on, for example, a case where information on the height of detection camera 1 from the predetermined surface indicates a small value (for example, 3 [m]) or a great value (for example, 100 [m]), and thus it is possible to further improve detection accuracy of a specified substance in nonvisible light sensor NVSS, also in consideration of errors when nonvisible light sensor NVSS detects a distance. In addition, display control unit 37 can generate display data as an example of the information regarding a specified substance, also in consideration of errors according to a height at which detection camera 1 is installed when detection processing unit 27 detects a distance.

Control unit 11 sets a detection threshold value M of the specified substance of detection processing unit 27 of nonvisible light sensor NVSS in distance detection/substance detection processing portion 27*a* of detection processing unit 27 (step S3). The detection threshold value M is preferably set to a value suitable for a specified substance which is a detection target.

After step S3, control unit 11 outputs a control signal for starting an imaging process to each constituent element of visible light camera VSC (step S4-1), and outputs light source scanning timing signal TR for causing first projection light source 13 or second projection light source 15 to start projecting projection light LS1 or projection light LS2, to first projection light source 13 and second projection light source 15 of nonvisible light sensor NVSS (step S4-2). One of the operation in step S4-1 and the operation in step S4-2 may be performed earlier.

Figure 5:
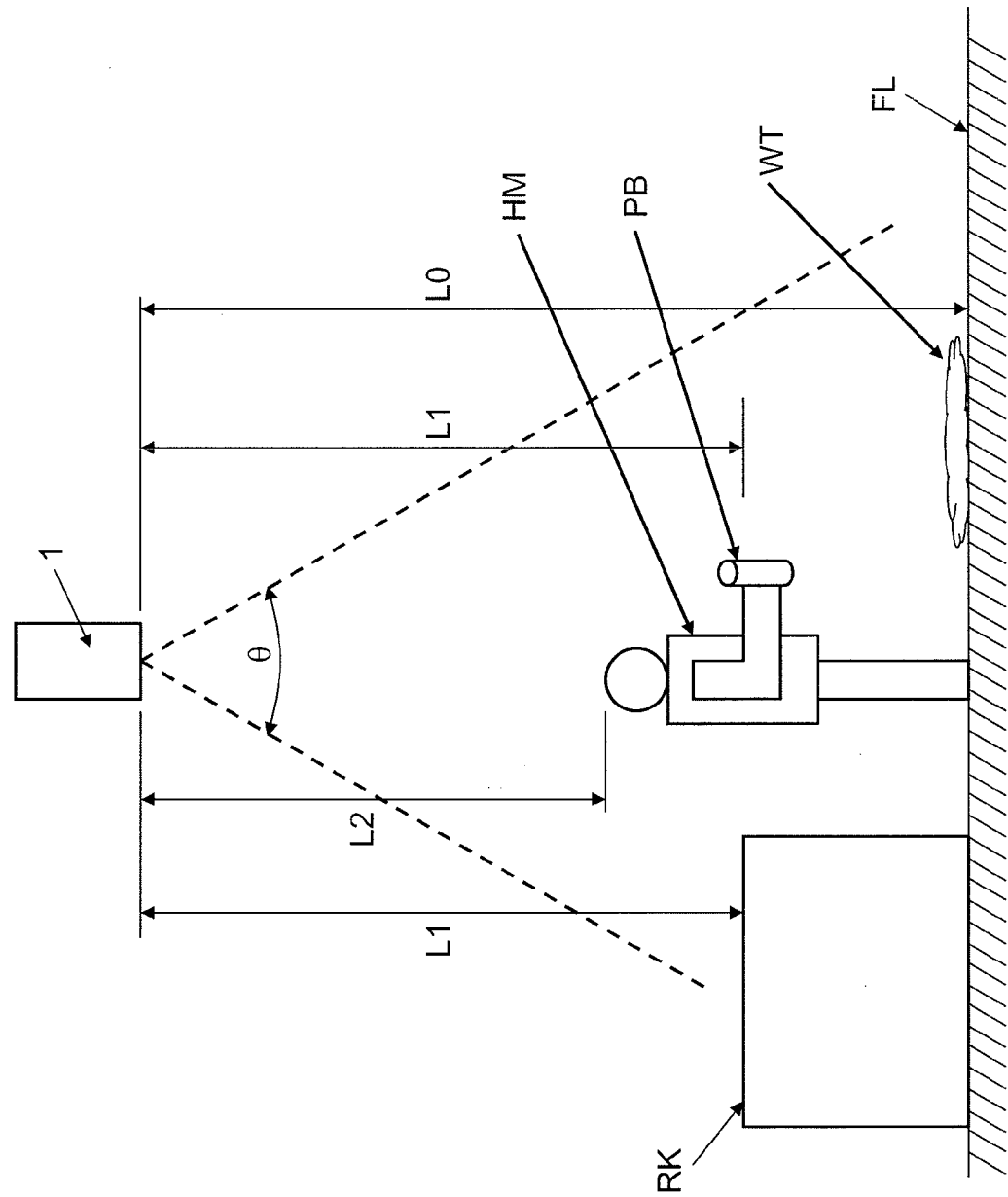
FIG. 5 is a diagram illustrating an example of a positional relationship between the detection camera of the present exemplary embodiment, and a puddle, a rack, and a person which are detection targets of the detection camera.

Next, with reference to FIG. 5, a description will be made of a positional relationship between detection camera 1, and person HM, a rack RK, and puddle WT present in the detection region, by using puddle WT as an example of a specified substance which is a detection target of detection camera 1 of the present exemplary embodiment. FIG. 5 is a diagram illustrating an example of a positional relationship between detection camera 1 of the present exemplary embodiment, and puddle WT which is a detection target of detection camera 1, rack RK, and person HM.

In the detection region illustrated in FIG. 5, detection camera 1 is installed at a position (for example, a ceiling surface) of a distance L0 from a predetermined surface (for example, floor FL; which is the same for the following). Person HM stands on floor FL, and rack RK is placed thereon. Person HM holds a beverage PB, a distance from detection camera 1 to each of the beverage PB and rack RK is L1. A distance from detection camera 1 to the head of person HM is L2. In addition, there is puddle WT on floor FL.

Detection camera 1 images person HM, rack RK, and puddle WT present in a range of an angle of view θ with visible light camera VSC, and generates visible light camera image data including person HM, rack RK, and puddle WT (refer to FIG. 6). FIG. 6 is a diagram illustrating an example of visible light camera image data generated by visible light camera VCS of detection camera 1 of the present exemplary embodiment. Here, it is difficult to determine the presence of puddle WT in the visible light camera image data of visible light camera VSC (refer to the dotted puddle WT illustrated in FIG. 6).

Detection camera 1 generates substance position image data regarding floor FL located at the position of which a distance from detection camera 1 is L0, the beverage PB and rack RK of which distances from detection camera 1 are L1, and the head of person HM of which a distance from detection camera 1 is L2, with nonvisible light sensor NVSS.

Figure 8:
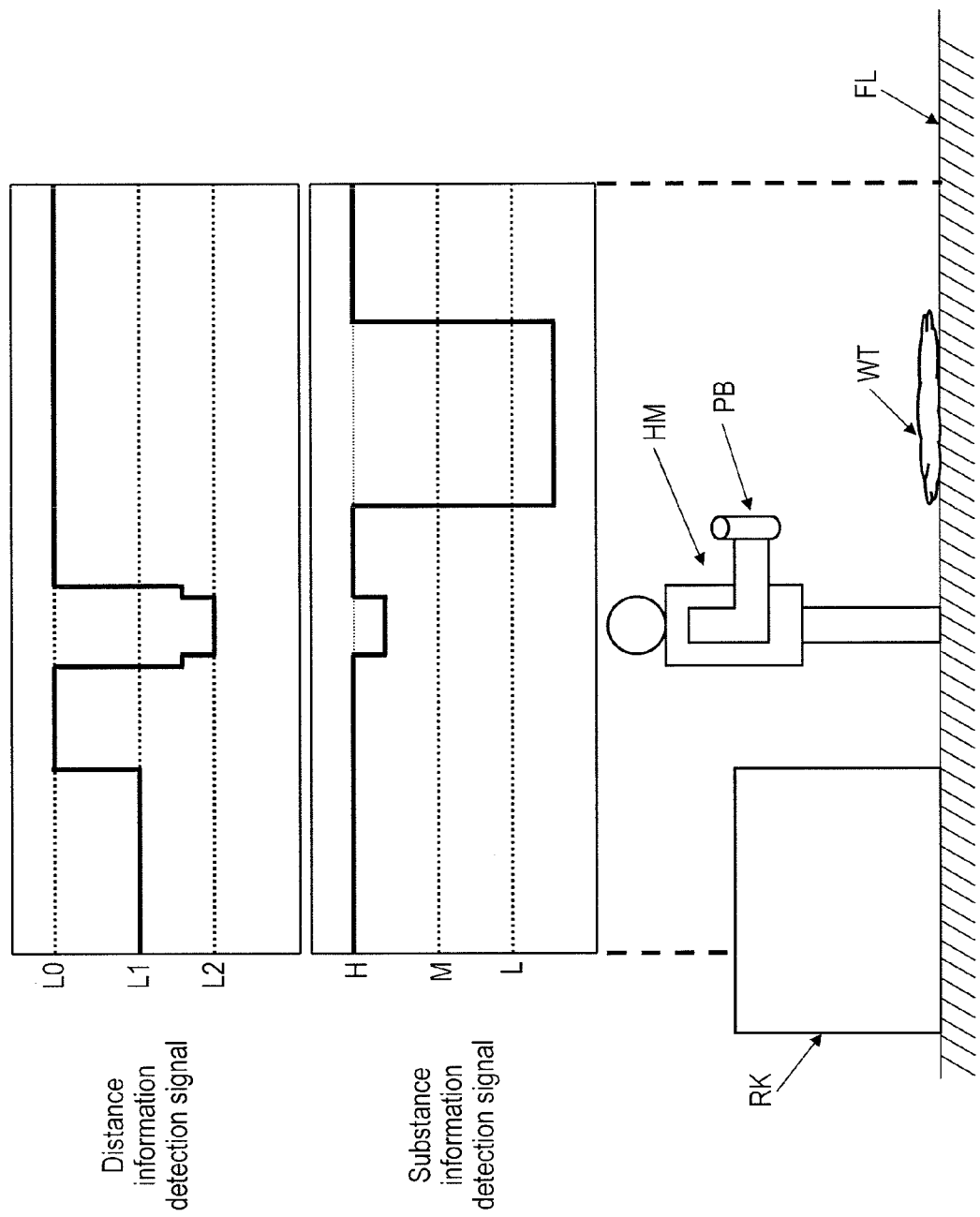
FIG. 8 is a diagram illustrating a comparison between a distance information detection signal and a substance information detection signal in a cross section taken along the line VIII-VIII of FIG. 6.

FIG. 8 is a diagram illustrating a comparison between a distance information detection signal and a substance information detection signal in a cross section taken along the line VIII-VIII of FIG. 6. The distance information detection signal and the substance information detection signal illustrated in FIG. 8 are signals which are output from distance detection/substance detection processing portion 27*a* to detection result filtering portion 27*c*. Detection result filtering portion 27*c* determines that a specified substance (in the present exemplary embodiment, water such as puddle WT) is detected at the position of which a distance from detection camera 1 is L0 in the detection region in a case where a level of the substance information detection signal is equal to or lower than the detection threshold value M, by using the detection threshold value M which is set by control unit 11 in step S3 illustrated in FIG. 4. In other words, since projection light LS2 with the second wavelength (for example, 1.45 μm) is absorbed in puddle WT, the intensity (amplitude) of reflected light RV2 of projection light LS2 attenuates more than the intensity (amplitude) of reflected light RV1 of projection light LS1. Therefore, in FIG. 8, a level of the substance information detection signal at the position of puddle WT with the distance L0 is considerably lower than levels of the substance information detection signals at the other positions. Since water is considered to be also included in the head of person HM, a level of the substance information detection signal of person HM with distance L2 is slightly lower than levels of the substance information detection signals at the other positions.

Detection result filtering portion 27*c* may extract a detection result of the substances in the detection region for each distance, detected by distance detection/substance detection processing portion 27*a*, by using an output from distance detection/substance detection processing portion 27*a*, and may output the extracted detection result to display processing unit 29. In this case, display processing unit 29 generates substance position image data indicating detection results of the substances in the detection region for each distance by using the output from detection result filtering portion 27*c* (refer to FIGS. 9 to 14).

Figure 9:
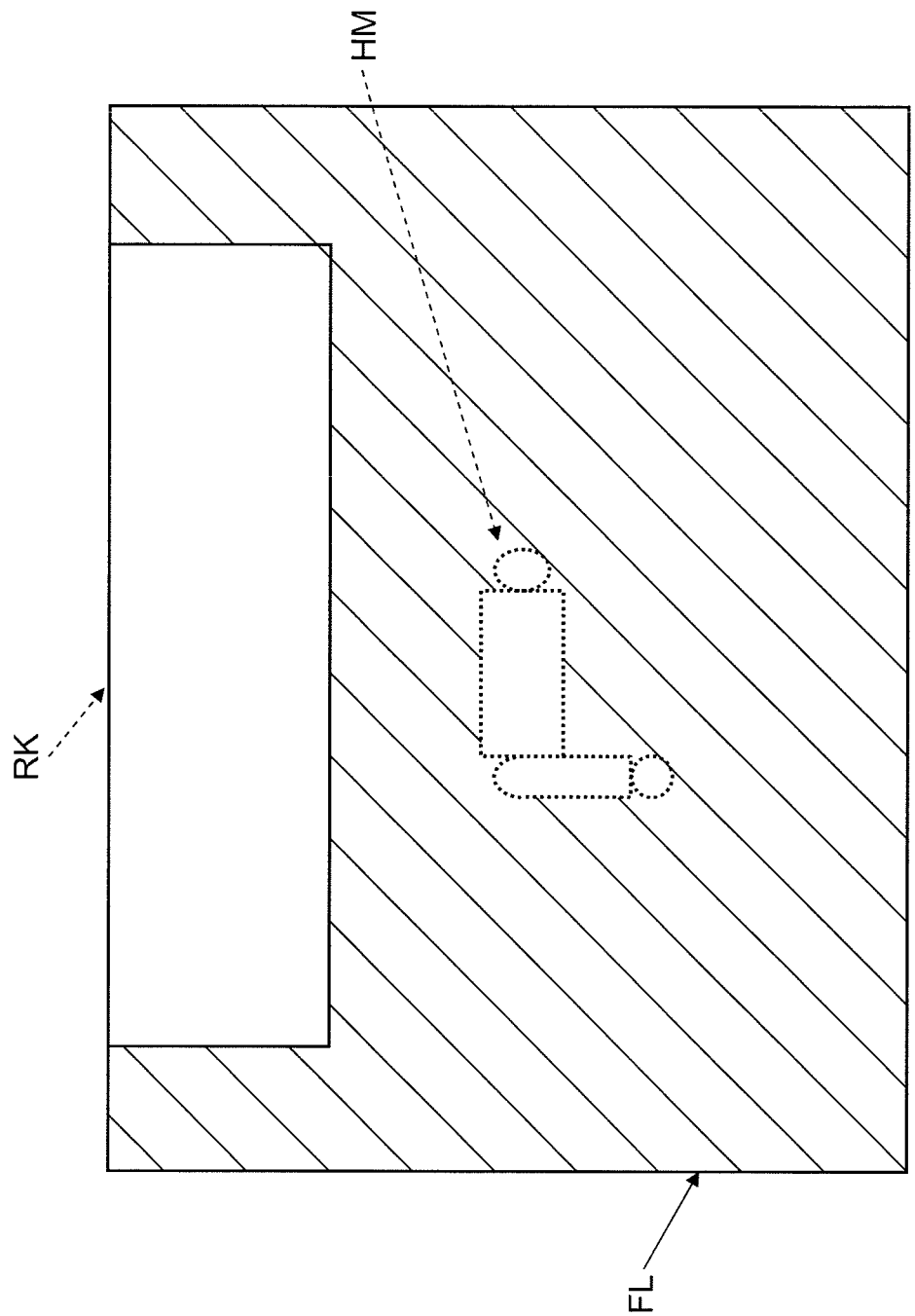
FIG. 9 is a diagram illustrating an example of substance position image data at a distance of L0 from the nonvisible light sensor of the detection camera of the present exemplary embodiment.
Figure 10:
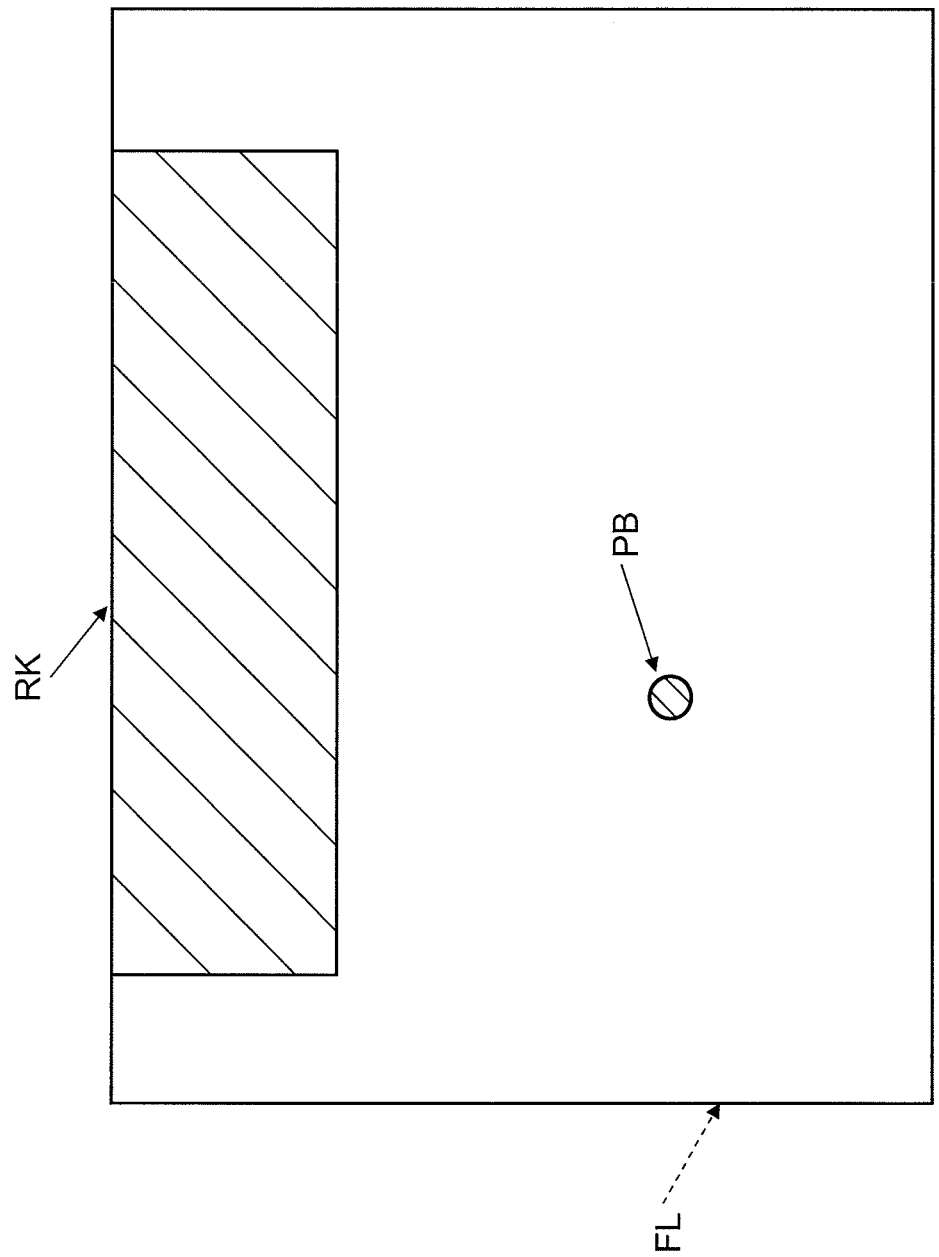
FIG. 10 is a diagram illustrating an example of substance position image data at a distance of L1 from the nonvisible light sensor of the detection camera of the present exemplary embodiment.
Figure 11:
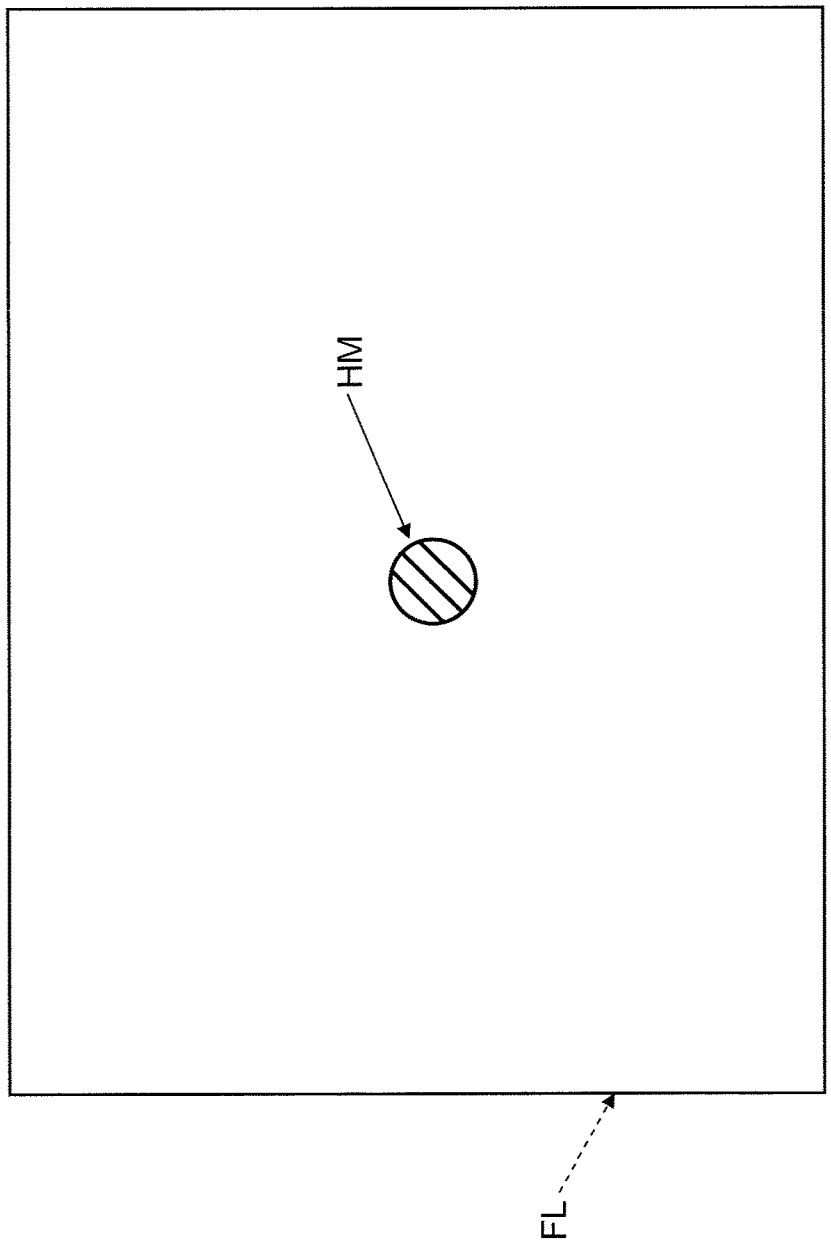
FIG. 11 is a diagram illustrating an example of substance position image data at a distance of L2 from the nonvisible light sensor of the detection camera of the present exemplary embodiment.
Figure 12:
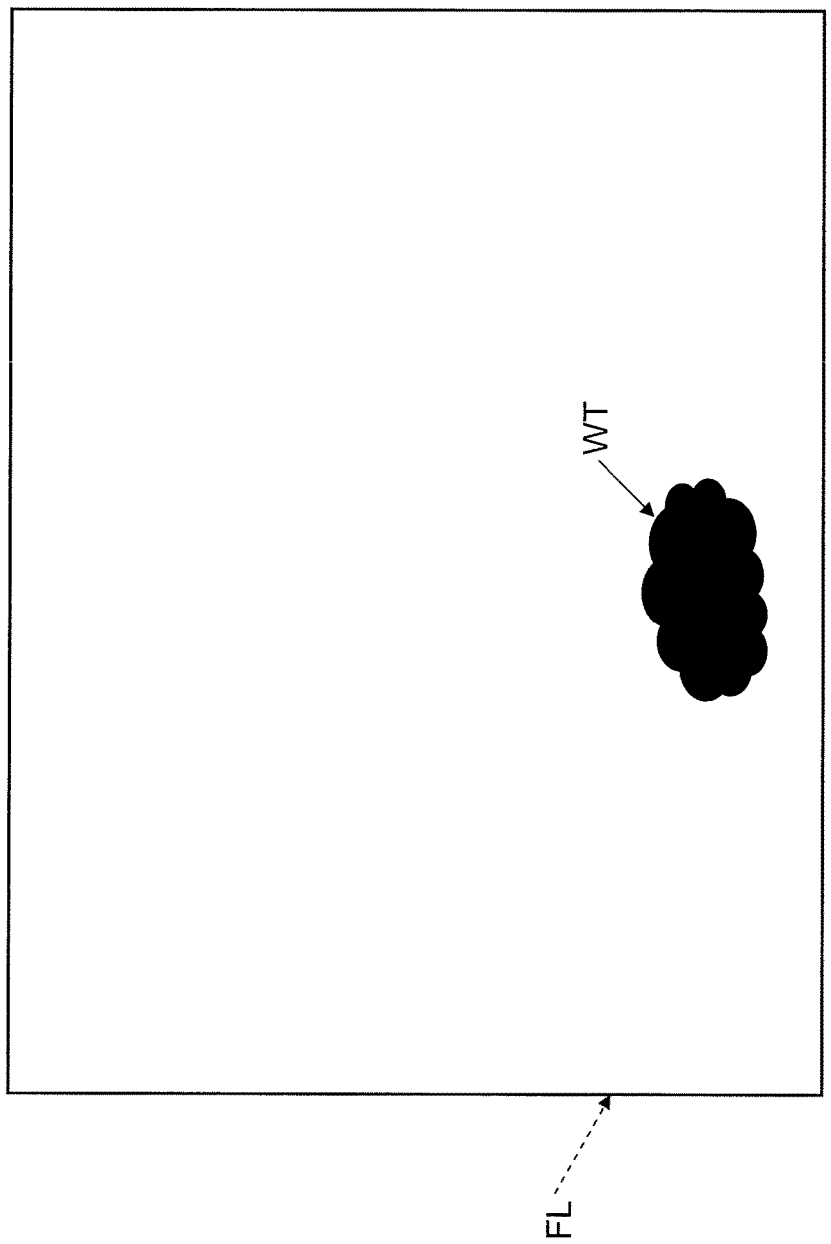
FIG. 12 is a diagram illustrating an example of substance position image data indicating a substance detection result at the distance of L0 from the nonvisible light sensor of the detection camera of the present exemplary embodiment.
Figure 13:
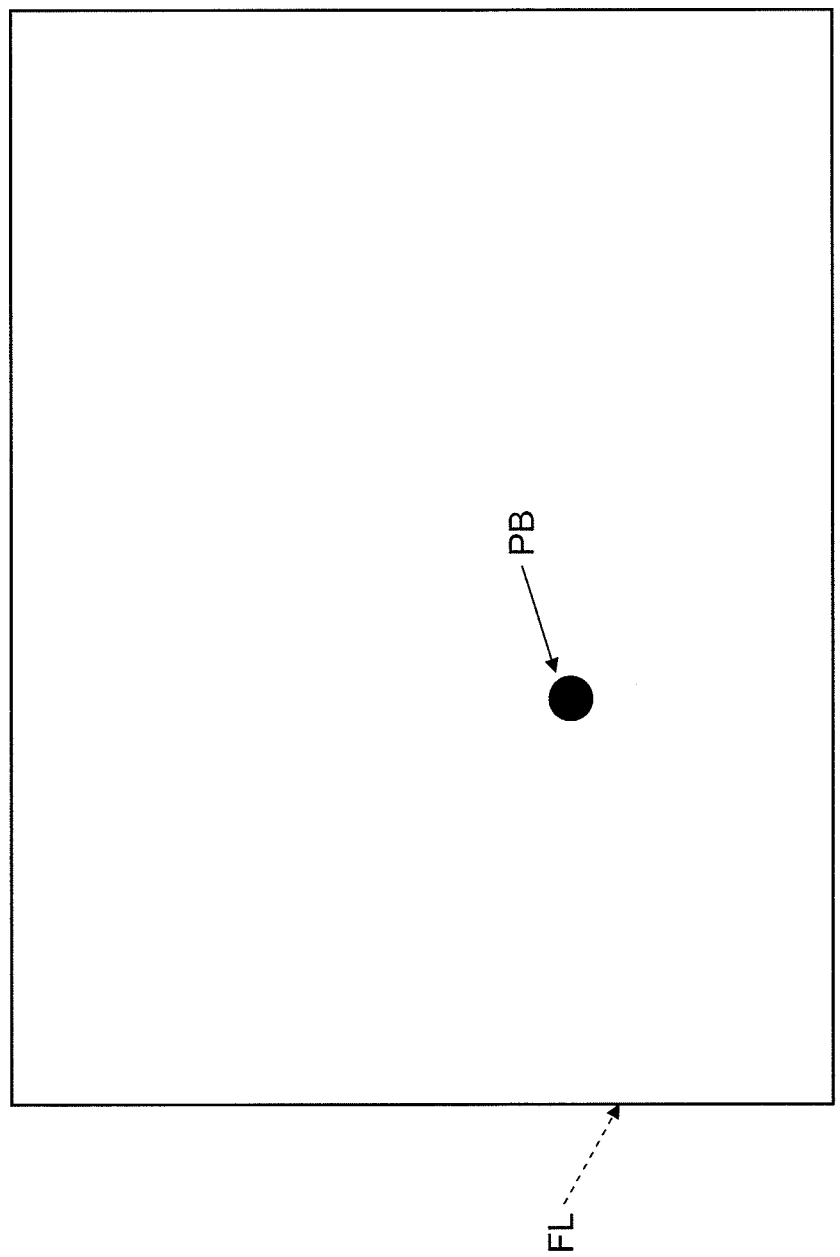
FIG. 13 is a diagram illustrating an example of substance position image data indicating a substance detection result at the distance of L1 from the nonvisible light sensor of the detection camera of the present exemplary embodiment.

FIG. 9 is a diagram illustrating an example of substance position image data at the distance L0 from nonvisible light sensor NVSS of detection camera 1 of the present exemplary embodiment. FIG. 10 is a diagram illustrating an example of substance position image data at distance L1 from the nonvisible light sensor of the detection camera of the present exemplary embodiment. FIG. 11 is a diagram illustrating an example of substance position image data at distance L2 from the nonvisible light sensor of the detection camera of the present exemplary embodiment. FIG. 12 is a diagram illustrating an example of substance position image data indicating a substance detection result at the distance L0 from the nonvisible light sensor of the detection camera of the present exemplary embodiment. FIG. 13 is a diagram illustrating an example of substance position image data indicating a substance detection result at distance L1 from the nonvisible light sensor of the detection camera of the present exemplary embodiment. FIG. 14 is a diagram illustrating an example of substance position image data indicating a substance detection result at distance L2 from the nonvisible light sensor of the detection camera of the present exemplary embodiment.

FIG. 9 illustrates substance position image data (refer to a hatched part illustrated in FIG. 9) indicating the position (specifically, floor FL) of which a distance from detection camera 1 is L0. The head and the arms of person HM, and the beverage PB are not present at the position of which a distance from detection camera 1 is L0, and thus are not shown in the substance position image data illustrated in FIG. 9 (refer to the dotted lines illustrated in FIG. 9). FIG. 10 illustrates substance position image data (refer to a hatched part illustrated in FIG. 10) indicating the position (specifically, rack RK and the beverage PB) of which a distance from detection camera 1 is L1. FIG. 11 illustrates substance position image data (refer to a hatched part illustrated in FIG. 11) indicating the position (specifically, the head of person HM) of which a distance from detection camera 1 is L2.

FIG. 12 illustrates substance position image data (a black part illustrated in FIG. 12) indicating that puddle WT is detected at the position of which the distance from detection camera 1 is L0. FIG. 13 illustrates substance position image data (a black part illustrated in FIG. 13) indicating that the beverage PB is detected at the position of which the distance from detection camera 1 is L1. In this case, a level of substance information detection signal of the beverage PB is substantially equivalent to a level of substance information detection signal of puddle WT. FIG. 14 illustrates substance position image data at the position of which the distance from detection camera 1 is L2, but a level of a substance information detection signal of the head of person HM is higher than the detection threshold value M, and thus the head of person HM is not displayed in the substance position image data.

Figure 17:
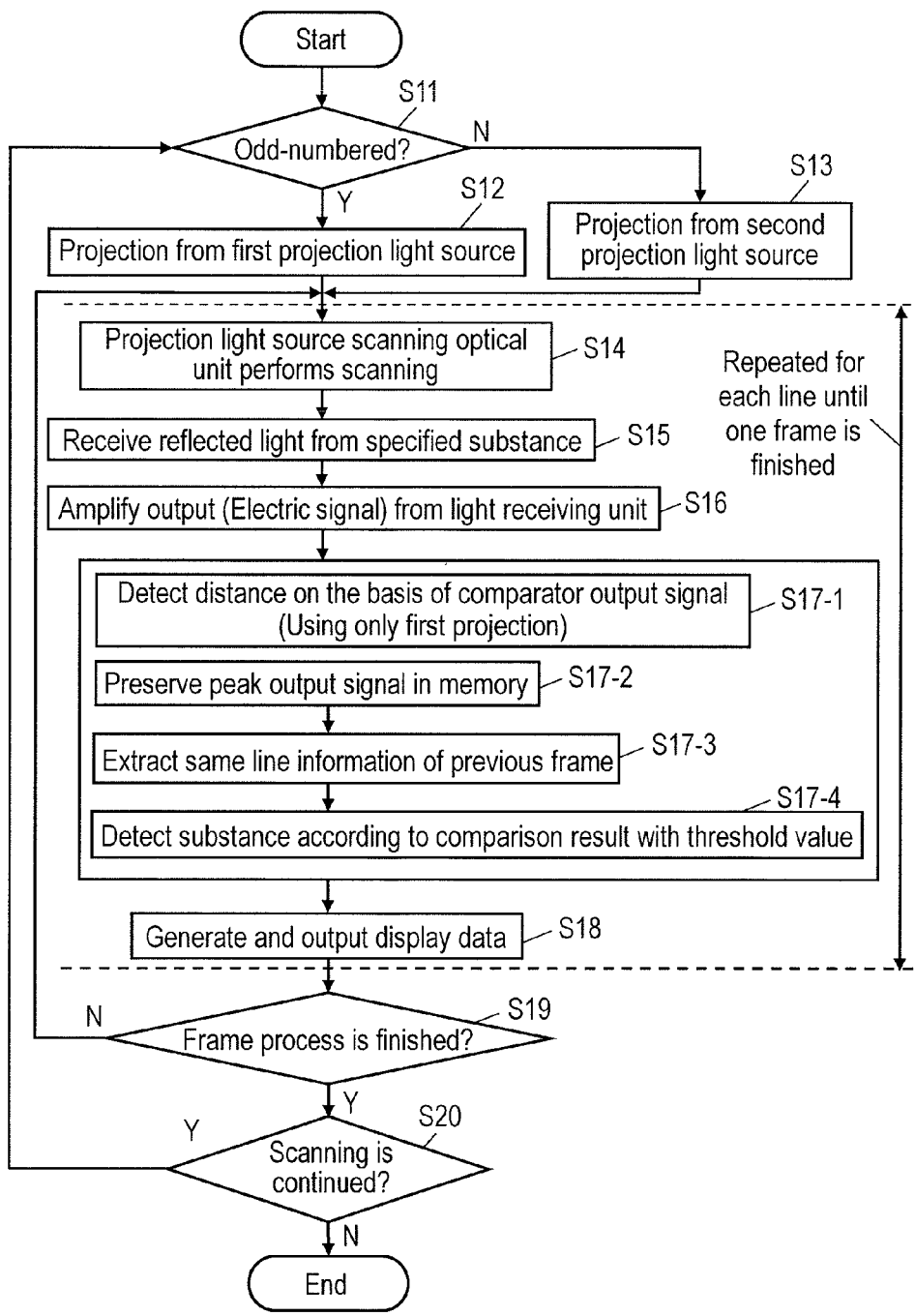
FIG. 17 is a flowchart illustrating specific operation procedures of substance detection in the nonvisible light sensor of the detection camera of the present exemplary embodiment.

Description of Specific Operation of Substance Detection in Nonvisible Light Sensor Next, with reference to FIG. 17, a description will be made of specific operation procedures of substance detection in nonvisible light sensor NVSS of detection camera 1. FIG. 17 is a flowchart illustrating specific operation procedures of substance detection in nonvisible light sensor NVSS of detection camera 1 of the present exemplary embodiment. On the premise of description of the flowchart illustrated in FIG. 17, timing control portion 11a outputs light source scanning timing signal TR to first projection light source 13 and second projection light source 15.

In FIG. 17, if light source emission signal RF is output from timing control portion 11a in an odd-numbered projection cycle (Y in step S11), first projection light source 13 projects projection light LS1 with the first wavelength (for example, 1.1 μm) in response to light source emission signal RF from timing control portion 11a (step S12). Projection light source scanning optical unit 17 scans predetermined lines of the detection region with projection light LS1 in a one-dimensional manner (step S14). In a case where a specified substance is present on the predetermined lines of the detection region, reflected light RV1 which is a result of projection light LS1 being reflected from the specified substance is received by light receiving unit 23 via imaging optical unit 21 (step S15).

In signal processing unit 25, an output (electric signal) of reflected light RV1 from light receiving unit 23 is converted into a voltage signal, and a level of the voltage signal is amplified to a level which can be processed by comparator/peak holding portion 25c (step S16). Comparator/peak holding portion 25c binarizes an output signal from amplification circuit 25b according to a comparison result between the output signal from amplification circuit 25b with a predetermined threshold value, and outputs an obtained result to distance detection/substance detection processing portion 27a. Comparator/peak holding portion 25c outputs information on a peak of the output signal from amplification circuit 25b to distance detection/substance detection processing portion 27a.

Distance detection/substance detection processing portion 27a measures a distance from detection camera 1 to a specified substance on the basis of an output (binarized signal) from comparator/peak holding portion 25c for reflected light RV1 of projection light LS1 with the first wavelength (for example, 1.1 μm) (step S17-1).

Distance detection/substance detection processing portion 27a temporarily preserves the output (peak information) from comparator/peak holding portion 25c for reflected light RV1 of projection light LS1 with the first wavelength, in memory 27b (step S17-2). Distance detection/substance detection processing portion 27a reads the output from comparator/peak holding portion 25c regarding the same line, for reflected light RV1 or reflected light RV2 of projection light LS1 or projection light LS2 with the first or second wavelength in the previous frame (projection cycle) preserved in memory 27b, from memory 27b (step S17-3). Distance detection/substance detection processing portion 27a determines whether or not the specified substance is detected in the detection region on the basis of the output (peak information) from comparator/peak holding portion 25c for reflected light RV1 of projection light LS1 with the first wavelength, the output (peak information) from comparator/peak holding portion 25c for reflected light RV2 of projection light LS2 with the second wavelength, and a predetermined detection threshold value (for example, the detection threshold value M) in the same line of the detection region (step S17-4). On the basis of the output from distance detection/substance detection processing portion 27a and a predetermined detection target distance or detection target distance range designated by control unit 11, detection result filtering portion 27c filters and extracts information regarding the specified substance of which a distance from detection camera 1 is in the detection target distance or the detection target distance range.

Display processing unit 29 generates substance position image data indicating a position of the specified substance in the detection region for each distance from detection camera 1 by using the output from detection result filtering portion 27c, as an example of the information regarding the specified substance of which a distance from detection camera 1 in the detection region is in the detection target distance or the detection target distance range (step S18). The respective operations in steps S14, S15, S16, S17-1 to S17-4, and S18 are performed for each line in the detection region during one frame (projection cycle).

After step S18, if execution of the respective operations in steps S14, S15, S16, S17-1 to S17-4, and S18 is not completed for all lines in the detection region (No in step S19), the respective operations in steps S14, S15, S16, S17-1 to S17-4, and S18 are repeatedly performed until execution of the respective operations in steps S14, S15, S16, S17-1 to S17-4, and S18 is completed for all the lines in the detection region.

On the other hand, if execution of the respective operations in steps S14, S15, S16, S17-1 to S17-4, and S18 is completed for all the lines in the detection region (Y in step S19), an operation of nonvisible light sensor NVSS returns to step S11 if the projection light is continuously scanned (Y in step S20). If the scanning of the projection light is not continued (N in step S20), the operation of nonvisible light sensor NVSS is finished.

Description of Generation of Display Data

Figure 18:
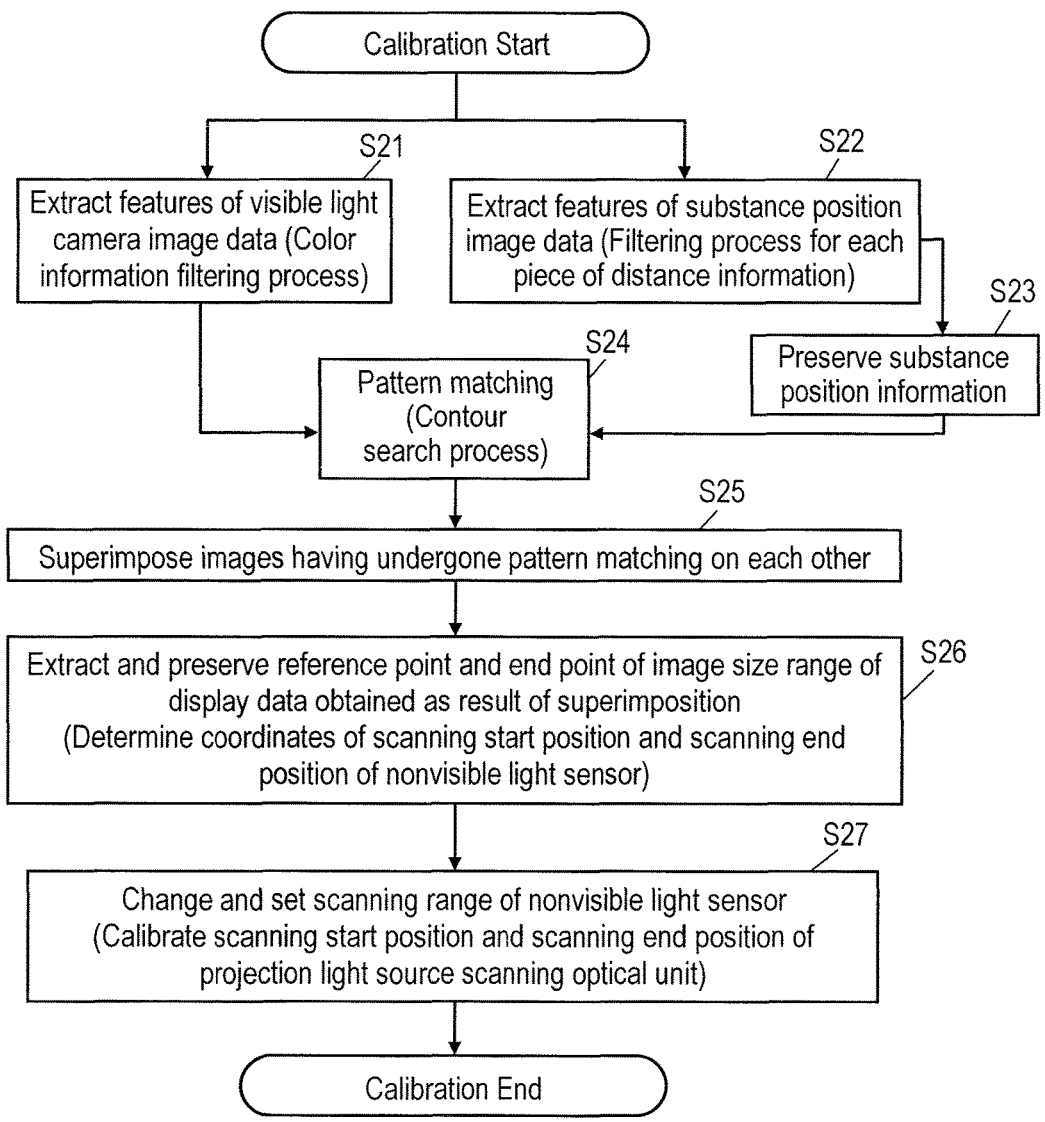
FIG. 18 is a flowchart illustrating an example of specific operation procedures for calibrating image size in a display control unit of the visible light camera of the detection camera of the present exemplary embodiment.

Next, a detailed description will be made of a generation process of display data in display control unit 37 with reference to FIGS. 18 and 19. FIG. 18 is a flowchart illustrating an example of specific operation procedures of calibrating an image size in display control unit 37 of the visible light camera VSC of detection camera 1 of the present exemplary embodiment. FIG. 19 is a flowchart illustrating an example of operation procedures of indicating that a specified substance has been detected in a detection target distance range or of generating display data in the display control unit of the visible light camera of the detection camera of the present exemplary embodiment.

Detection camera 1 of the present exemplary embodiment has a configuration in which visible light camera VSC and nonvisible light sensor NVSS are integrally formed with each other, but configurations of the other constituent elements except for display control unit 37 of visible light camera VSC of the present exemplary embodiment are the same as those of an existing monitoring camera. In this case, nonvisible light sensor NVSS of detection camera 1 of the present exemplary embodiment is configured to be added to the existing visible light camera VSC. Therefore, there may be a case where an aspect ratio of visible light camera image data captured by visible light camera VSC does not match an aspect ratio of substance position image data generated by nonvisible light sensor NVSS. In a calibration operation illustrated in FIG. 18, display control unit 37 makes an aspect ratio of visible light camera image data captured by visible light camera VSC match an aspect ratio of substance position image data generated by nonvisible light sensor NVSS.

In FIG. 18, display control unit 37 extracts features of the visible light camera image data, for example, through a filtering process using color information (step S21). In addition, the operation in step S21 may be performed by imaging signal processing unit 35, and, in this case, display control unit 37 acquires information on a feature extraction result of the visible light camera image data performed by imaging signal processing unit 35, from imaging signal processing unit 35.

Display control unit 37 extracts features of the substance position image data, for example, through a filtering process for each piece of distance information (step S22). The operation in step S22 may be performed by display processing unit 29, and, in this case, display control unit 37 acquires information on a feature extraction result of the substance position image data performed by display processing unit 29, from display processing unit 29. Display control unit 37 preserves information (substance position information) regarding a detected position of a substance in a memory (not illustrated) for a work memory on the basis of the information on the feature extraction result of the substance position image data obtained in step S22 (step S23).

Display control unit 37 searches for each contour of the visible light camera image data and the substance position image data so as to perform pattern matching by using the information on the feature extraction result of the visible light camera image data obtained in step S21 and the information on the feature extraction result of the substance position image data obtained in step S22 (step S24). Display control unit 37 superimposes the visible light camera image data and the substance position image data having undergone the pattern matching in step S24 on each other (step S25). Display control unit 37 can obtain display data in which aspect ratios of the visible light camera image data and the substance position image data match each other through the operations in steps S24 and 25.

Display control unit 37 extracts a reference point (for example, an origin) and an end point of an image size range of the display data obtained as a result of the superimposition in step S25 and preserves the extracted results in control unit 11 (step S26). In FIG. 2, for simplification of illustration, arrows are not illustrated between control unit 11 and display control unit 37. The reference point and the end point of the image size range of the display data respectively correspond to a scanning start position and a scanning end position of projection light from nonvisible light sensor NVSS.

After step S26, control unit 11 changes a scanning range of the projection light from nonvisible light sensor NVSS by using the information on the reference point (for example, an origin) and the end point of the image size range of the display data acquired from display control unit 37, and sets changed information on the scanning start position and the scanning end position of projection light source scanning optical unit 17, in projection light source scanning optical unit 17 (step S27). The calibration operation illustrated in FIG. 18 is performed once, and thus display control unit 37 can easily generate the display data in which an aspect ratio of the visible light camera image data from visible light camera VSC matches an aspect ratio of the substance position image data from nonvisible light sensor NVSS.

In FIG. 19, display control unit 37 acquires the visible light camera image data from imaging signal processing unit 35 and the substance position image data for each distance from display processing unit 29 (step S31). Display control unit 37 determines whether or not a specified substance is detected in the predetermined detection region (refer to FIG. 5) of detection camera 1 on the basis of the substance position image data for each distance from display processing unit 29 (step S32). If the specified substance is not detected in the detection region (N in step S32), an operation of display control unit 37 returns to step S31.

On the other hand, if the specified substance is detected in the detection region (Y in step S32), display control unit 37 determines whether or not the detected specified substance is present in a detection target distance or a detection target distance range (step S33). If it is determined that the specified substance is not present in the detection target distance or the detection target distance range (N in step S33), an operation of display control unit 37 returns to step S31.

On the other hand, if it is determined that the specified substance is present in the detection target distance or the detection target distance range (Y in step S33), an operation of display control unit 37 performs at least one of, for example, alerting to the presence using sound or the like, emphasis display indicating that the specified substance has been detected, and combination with a visible light camera image (that is, generation of display data) (step S34). If the operation is not continued (Y in step S35), the detection operation is finished. The above description relates to the flowchart illustrated in FIG. 19.

As mentioned above, in detection camera 1 of the present exemplary embodiment, visible light camera VSC acquires visible light camera image data through imaging, and nonvisible light sensor NVSS alternately projects the first projection light LS1 with the first wavelength (for example, 1.1 µm) and the second projection light LS2 with the second wavelength (for example, 1.45 µm) for each predetermined projection cycle so as to scan a detection region with projection light LS1 and projection light LS2 in a two-dimensional manner. Detection camera 1 detects a distance from detection camera 1 to a specified substance on the basis of a time difference between the time when projection light LS1 is projected and the time when reflected light RV1 which is a result of projection light LS1 being reflected from the specified substance is received. In addition, detection camera 1 determines whether or not the specified substance is detected in the detection region on the basis of reflected light RV1 and reflected light RV2 which is a result of projection light LS2 being reflected from the specified substance.

In a case where the specified substance is detected at a distance which is in a predetermined detection target distance or detection target distance range from detection camera 1 in the detection region, detection camera 1 generates substance position image data indicating that the specified substance is detected in the detection region. In other words, detection camera 1 selects whether or not the specified substance detected in the detection region is displayed on the basis of the detection target distance or the detection target distance range. In addition, the specified substance (a desired specified substance) which is selected to be displayed is generated as substance position image data. Detection camera 1 generates display data in which the visible light camera image data is combined with the substance position image data, and outputs the display data to an external connection apparatus (for example, camera server CS or communication terminal MT).

Consequently, even in a case where a specified substance (for example, puddle WT), which is hardly identified at a glance in visible light camera image data obtained by visible light camera VSC having an angle of view including a predetermined detection region, is present in the detection region, detection camera 1 can generate display data in which substance position image data for each distance from detection camera 1, obtained by nonvisible light sensor NVSS, is combined with the visible light camera image data. As mentioned above, the specified substance which is displayed through the combination with the visible light camera image data is selected according to information on the distance to the detected specified substance, and thus only the desired specified substance can be displayed. In other words, it is possible to prevent a specified substance which is not desired from being displayed. Thus, detection camera 1 can improve detection accuracy of a specified substance which is hardly identified at a glance in the visible light camera image data, for each distance from detection camera 1 in a predetermined detection region. For this reason, a user can be notified of a detection result of the presence of absence of a desired specified substance, and thus it is possible to minimize a user's incorrect recognition regarding the presence or absence of the desired specified substance.

In the above-described present exemplary embodiment, an image output apparatus according to the present invention has been described by exemplifying detection camera 1, but the image output apparatus according to the present invention may not include constituent elements as the imaging unit such as imaging optical unit 31, light receiving unit 33, and imaging signal processing unit 35 of visible light camera VSC. For example, as long as the image output apparatus may hold one or more items of visible light camera image data (for example, map data or picture data) in advance, and includes display control unit 37 of visible light camera VSC of detection camera 1 and nonvisible light sensor NVSS of detection camera 1, even if the constituent elements as the imaging unit such as imaging optical unit 31, light receiving unit 33, and imaging signal processing unit 35 are omitted, the same effect as that in detection camera 1 of the above-described present exemplary embodiment can be achieved. In addition, it is possible to reduce the number of components of the image output apparatus and thus to minimize an increase in manufacturing cost of the image output apparatus. In addition, the image output apparatus may include the constituent elements as the imaging unit such as imaging optical unit 31, light receiving unit 33, and imaging signal processing unit 35 of visible light camera VSC. Consequently, even if one or more items of visible light camera image data (for example, map data or picture data) are not held in advance, the image output apparatus can achieve the same effect as that in detection camera 1 of the above-described present exemplary embodiment.

In the above-described present exemplary embodiment, a specified substance has been described by exemplifying water such as puddle WT, but a specified substance which can be detected by detection camera 1 is not limited to water, and may be ones shown in the following Table 1. Table 1 shows specified substances which can be detected by detection camera 1, and use wavelengths of projection light used in first projection light source 13 or second projection light source 15 in order to detect the specified substances. Therefore, detection camera 1 can detect not only water but also a plurality of types of specified substances according to use wavelengths of projection light, and can generate and output display data in which visible light camera image data is combined with substance position image data indicating that a specified substance has been detected.

TABLE 1

| Specified substances | Main use wavelengths |
| --- | --- |
| Chlorophyll | 0.44 µm, 0.68 µm |
| Hemoglobin (HB) | 0.66 µm |
| Protein | 1.19 µm |
| Water ($H_2O$) | 1.45 µm |
| Plastics | 1.7 µm |
| Sugar | 2.1 µm |
| Carbon dioxide ($CO_2$) | 2.8 µm |
| Methane gas ($CH_4$) | 3.3 µm |

The above-described detection target distance range may be set not alone but in plurality. For example, the detection target distance range includes a first range of 2 to 3 [m] and a second range of 6 to 8 [m]. Similarly, the above-described detection target distance may be set not to a single value but to a plurality of values. In a case where a plurality of detection target distances are input, control unit 11 may calculate and set a detection target distance range corresponding to each detection target distance. As mentioned above, a plurality of detection target distances or detection target distance ranges can be set, and thus it is possible to set detection conditions of detection camera 1 according to circumstances in which detection camera 1 is installed. For example, in FIG. 8, in a case where not only water on floor FL but also water on rack RK is desired to be detected, it is possible to set a detection target distance or a detection target distance range corresponding to each position. Therefore, it is possible to minimize incorrect detection of a specified substance.

In addition, the number of detection target distances or detection target distance ranges may be arbitrarily increased or decreased. Consequently, it is possible to set detection conditions of detection camera 1 according to complexity of circumstances in which detection camera 1 is installed. For example, in a case where circumstances are complex (for example, in a case where a plurality of racks RK are present), a large number of detection target distances or detection target distance ranges are set, and in a case where circumstances are simple (for example, in a case where there is no rack RK), a small number of detection target distance or detection target distance range are set.

Such a plurality of detection target distances or detection target distance ranges may be set in advance, and may be arbitrarily set by a user using camera server CS, communication terminal MT, or the like. Alternatively, detection camera 1 may be provided with an input unit which allows the plurality of detection target distances or detection target distance ranges to be set. Regarding the detection target distance range, both of the upper and lower limits are not required to be set unlike in the above-described specific example, and at least one limit may be set. For example, a detection target distance range such as 100 [m] or more, or such as 5 [m] or less, may be set.

In the present exemplary embodiment, a description has been made of a case where first projection light source 13 performs projection in the odd-numbered projection cycle, and second projection light source 15 performs projection in the even-numbered projection cycle, but first projection light source 13 and second projection light source 15 may not perform projection alternately for each projection cycle. For example, timings may be changed so that first projection light source 13 and second projection light source 15 perform projection in different projection cycles or random projection cycles. In addition, in a case where a plurality of (for example, two) imaging optical units 21 and light receiving units 23 are provided in detection camera 1, projection light LS1 from first projection light source 13 and projection light LS2 from second projection light source 15 may be simultaneously projected.

In the present exemplary embodiment, a description has been made of detection camera 1 in which projection section PJ, image determination section JG, and visible light camera VSC are integrally formed with each other, but projection section PJ, image determination section JG, and visible light camera VSC may be provided separately from each other. For example, projection section PJ and image determination section JG may be held in different casings. Similarly, projection section PJ and visible light camera VSC may be held in different casings. In addition, first projection light source 13 and second projection light source 15 may be provided separately from each other.

However, image determination section JG and visible light camera VSC are preferably provided in the same casing, as in the present exemplary embodiment. More specifically, imaging optical unit 21 used to form substance position image data and imaging optical unit 31 used to form visible light camera image data are preferably provided in the same casing. The imaging optical units 21 and 31 are provided in the same casing, and thus light reception positions of the light receiving units of the two units can be made close to each other. In other words, detection positions of substance position image data and visible light camera image data can be made close to each other. Consequently, a deviation between the substance position image data and the visible light camera image data can be reduced, and thus it is possible to reduce a load of a combination process (for example, the pattern matching in step S24 or the image superimposition in step S25) of the visible light camera image data and the substance position image data performed by display control unit 37.

In addition, processes on a received signal may be performed by an external apparatus (for example, camera server CS or communication terminal MT) of detection camera 1. The signal processes correspond to processes performed by, for example, signal processing unit 25, detection processing unit 27, display processing unit 29, imaging signal processing unit 35, display control unit 37, control unit 11, and the like, described above. If functions regarding the signal processes are provided in an external apparatus of detection camera 1, detection camera 1 can be miniaturized.

Distance detection/substance detection processing portion 27a may use only a distance information detection signal. A distance information detection signal in an initial state is preserved in memory 27b and is compared with a distance information detection signal which is newly acquired, and thus difference information from distance information in the initial state can be obtained. The difference information may be used to detect intrusion of a person or the like, or used to detect carrying-away of goods. For example, since a difference occurs between distance information in an initial state in which person HM is not present on floor FL and distance information in a case where person HM intrudes on floor FL, the intrusion of person HM can be detected. Similarly, also in a case where rack RK provided on floor FL is carried away, difference information from distance information in an initial state is obtained, and thus the carrying-away can be detected.

Difference information on distance information is used, and thus it is possible to count the number of people or to monitor movement lines of the people. By using the difference information on distance information, a block of the difference information is identified as a person, and thus the number of people can be counted, or time transition of the distance information detection signal is processed by image determination section JG, and thus movement lines can be monitored. The information on the counting of the number of people or the monitoring of movement lines is input to display control unit 37 of visible light camera VSC and can thus be displayed on camera server CS or communication terminal MT.

Hereinafter, a description will be made of configurations of an image output apparatus, an image output method, and an image output system according to the above-described present invention.

An image output apparatus of the present invention includes: a detection unit that detects a specified substance; and a combining unit that outputs display data in which information regarding the specified substance is combined with image data in a case where the specified substance is detected at a predetermined position.

The image output apparatus of the present invention may further include an imaging unit that acquires the image data.

An image output apparatus of the present invention may include: a detection unit that detects a specified substance; an imaging unit that acquires image data; an acquisition unit that acquires distance information from the image output apparatus to the specified substance; and a combining unit that outputs display data in which information regarding the specified substance is combined with the image data in a case where the distance information is in a predetermined range.

The image output apparatus of the present invention may further include a calculation unit that calculates the predetermined range on the basis of set distance information which is set.

In the image output apparatus of the present invention, the calculation unit may calculate the set distance information or the predetermined range on the basis of installation condition information of the imaging unit which is input.

In the image output apparatus of the present invention, the installation condition information may include height information from at least a predetermined surface of the imaging unit.

In the image output apparatus of the present invention, the calculation unit may change the predetermined range depending on the height information.

In the image output apparatus of the present invention, the predetermined range may include a plurality of ranges.

In the image output apparatus of the present invention, the number of the plurality of ranges may be increased or decreased.

The image output apparatus of the present invention may further include: a first projection unit that outputs first projection light with a first wavelength at a first time point; and a first light receiving unit that receives first reflected light which is a result of the first projection light being reflected from the specified substance, at a second time point, and the acquisition unit may acquire the distance information on the basis of a time difference between the first time point and the second time point.

In the image output apparatus of the present invention, the detection unit may detect the specified substance on the basis of intensity of the first reflected light.

The image output apparatus of the present invention may further include: a first projection unit that outputs first projection light with a first wavelength; a second projection unit that outputs second projection light with a second wavelength; a light receiving unit that receives first reflected light or second reflected light which is a result of the first projection light or the second projection light being reflected from the specified substance. Here, the acquisition unit may acquire the distance information on the basis of a time difference between the output of the first projection light and the reception of the first reflected light, and the detection unit may detect the specified substance on the basis of intensity of the second reflected light, or an intensity difference between the first reflected light and the second reflected light.

An image output method for an image apparatus of the present invention includes: detecting a specified substance; acquiring image data; acquiring distance information from the image output apparatus to the specified substance; and outputting display data in which information regarding the specified substance is combined with the image data in a case where the distance information is in a predetermined range.

An image output system of the present invention includes: an image output apparatus; and an external connection apparatus, in which the image output apparatus includes: a detection unit that detects a specified substance; an imaging unit that acquires image data; an acquisition unit that acquires distance information from the imaging unit to the specified substance; and a combining unit that outputs display data in which information regarding the specified substance is combined with the image data in a case where the distance information is in a predetermined range which is input by the external connection apparatus.

The image output system may further include an input unit that allows the predetermined range to be input.

In the image output system according of the present invention, the input unit may allow a plurality of ranges to be input as the predetermined range.

In the image output system of the present invention, the input unit may allow the number of the plurality of ranges to be set.

As mentioned above, although the various embodiments have been described with reference to the drawings, needless to say, the present invention is not limited to the embodiments. It is obvious that a person skilled in the art can conceive of various modifications and alterations within the scope recited in the claims, and the modifications and alterations are understood to be naturally included in the technical scope of the present invention.

What is claimed is:

1. An image output apparatus, comprising:
    a first projection light source that outputs first projection light with a first wavelength;
    a second projection light source that outputs second projection light with a second wavelength;
    a light receiver that receives first reflected light or second reflected light which is a result of the first projection light or the second projection light being reflected from a specified substance;
    a detection processor that
        acquires distance information of the specified substance based on a time difference between the output of the first projection light and the reception of the first reflected light, and
        detects an identify of the specified substance based on an intensity of the second reflected light;
    a camera that acquires image data; and
    a display control circuit that outputs display data in which information regarding substance position image data is combined with the image data,
    wherein the substance position image data represents that the specified substance exists in a condition which meets distance information of the specified substance is in a predetermined range.

2. The apparatus of claim 1, further comprising:
    a processor that calculates the predetermined range based on set distance information which is set.

3. The apparatus of claim 2,
    wherein the processor calculates the set distance information or the predetermined range based on installation condition information of the camera which is input.

4. The apparatus of claim 3,
    wherein the installation condition information includes height information from at least a predetermined surface of the camera.

5. The apparatus of claim 4,
    wherein the processor changes the predetermined range depending on the height information.

6. The apparatus of claim 1,
    wherein the predetermined range includes a plurality of ranges.

7. The apparatus of claim 6,
    wherein a number of the plurality of ranges is increased or decreased.

8. An image output method for an image output apparatus, the method comprising:
    outputting first projection light with a first wavelength;
    outputting second projection light with a second wavelength;

receiving first reflected light or second reflected light which is a result of the first projection light or the second projection light being reflected from a specified substance;

acquiring distance information of the specified substance based on a time difference between the output of the first projection light and the reception of the first reflected light;

detecting an identity of the specified substance based on an intensity of the second reflected light;

acquiring image data;

outputting display data in which information regarding substance position image data is combined with the image data, wherein the substance position image data represents that the specified substance exists in a condition which meets distance information of the specified substance is in a predetermined range.

9. An image output system comprising:

an image output apparatus; and an external connection apparatus, wherein the image output apparatus includes:

a first projection light source that outputs first projection light with a first wavelength;

a second projection light source that outputs second projection light with a second wavelength;

a light receiver that receives first reflected light or second reflected light which is a result of the first projection light or the second projection light being reflected from a specified substance;

a detection processor that
  acquires distance information of the specified substance based on a time difference between the output of the first projection light and the reception of the first reflected light, and
  detects an identify of the specified substance based on an intensity of the second reflected light;

a camera that acquires image data; and a display control circuit that outputs display data in which information regarding substance position image data is combined with the image data, wherein the substance position image data represents that the specified substance exists in a condition which meets distance information of the specified substance is in a predetermined range, and wherein the predetermined range is input by the external connection apparatus.

10. The system of claim 9, further comprising:

an input that allows the predetermined range to be input.

11. The system of claim 10, wherein the input allows a plurality of ranges to be input as the predetermined range.

12. The system of claim 11, wherein the input allows a number of the plurality of ranges to be set.

13. The apparatus of claim 1, wherein the intensity of the second reflected light is calculated as an intensity difference between the first reflected light and the second reflected light.

14. The apparatus of claim 1, wherein the predetermined range includes a distance L1 and a distance L0, the distance L0 being longer than the distance L1, and if the distance information of the specified substance indicates a distance that is shorter than the distance L0 and longer than the distance L1, the substance position image data of the specific substance is determined to be different from substance position image data of a specified substance having distance information longer than L0.

15. The apparatus of claim 1, wherein if the distance information of the specified substance is outside of the predetermined range, the substance position image data of the specified substance is not combined with the image data.

16. The apparatus of claim 14, wherein, if the distance information of the specified substance is longer than the distance L0, the substance position image data of the specified substance is determined to indicate a puddle.

* * * * *